(12) United States Patent
Singh et al.

(10) Patent No.: US 9,585,615 B2
(45) Date of Patent: Mar. 7, 2017

(54) SYSTEMS AND METHODS FOR MEASURING PERFORMANCE PARAMETERS RELATED TO ORTHOPEDIC ARTHROPLASTY

(71) Applicant: MiRus LLC, Atlanta, GA (US)

(72) Inventors: Angad Singh, Marietta, GA (US); Philip Matthew Fitzsimons, Lilburn, GA (US)

(73) Assignee: MiRus LLC, Atlanta, GA (US)

(*) Notice: Subject to any disclaimer, the term of this patent is extended or adjusted under 35 U.S.C. 154(b) by 0 days.

(21) Appl. No.: 14/860,409

(22) Filed: Sep. 21, 2015

(65) Prior Publication Data

US 2016/0007909 A1    Jan. 14, 2016

Related U.S. Application Data

(63) Continuation of application No. PCT/US2013/068054, filed on Nov. 1, 2013.
(Continued)

(51) Int. Cl.
    *A61B 17/56*      (2006.01)
    *A61B 5/00*      (2006.01)
    (Continued)

(52) U.S. Cl.
    CPC .......... *A61B 5/4585* (2013.01); *A61F 2/4657* (2013.01); *A61B 5/1121* (2013.01);
    (Continued)

(58) Field of Classification Search
CPC ........... A61F 2002/4666; A61F 2/4657; A61B 5/4585
See application file for complete search history.

(56) References Cited

U.S. PATENT DOCUMENTS

| | | |
|---|---|---|
| 5,197,488 A | 3/1993 | Kovacevic |
| 5,470,354 A | 11/1995 | Hershberger |
| | (Continued) | |

FOREIGN PATENT DOCUMENTS

| | | |
|---|---|---|
| CN | 1431888 | 7/2003 |
| CN | 101262816 | 9/2008 |
| | (Continued) | |

OTHER PUBLICATIONS

International Search Report and Written Opinion of the EPO International Searching Authority from Application No. PCT/US2013/068054, dated Jan. 29, 2014.
(Continued)

*Primary Examiner* — Matthew Lawson
(74) *Attorney, Agent, or Firm* — Meunier Carlin & Curfman LLC

(57) ABSTRACT

A knee balancing system for measuring performance parameters associated with an orthopedic articular joint comprises a force sensing module and one or more inertial measurement units. The force sensing module comprises a housing that includes an articular surface having a medial portion and a lateral portion, each of which is substantially mechanically isolated from the other. The force sensing module also includes first and second sets of sensors disposed within the housing. The first set of sensors is mechanically coupled to the medial portion of the articular surface and configured to detect information indicative of a first force incident upon the medial portion of the articular surface. The second set of sensors is mechanically coupled to the lateral portion of the articular surface and configured to detect information indicative of a second force incident upon a lateral portion of the articular surface. The inertial measurement unit is configured to detect information indicative of an orientation of at least one of a first bone and a second bone of a knee joint.

14 Claims, 18 Drawing Sheets

Related U.S. Application Data

(60) Provisional application No. 61/803,665, filed on Mar. 20, 2013.

(51) Int. Cl.
  *A61F 2/46* (2006.01)
  *A61B 5/11* (2006.01)

(52) U.S. Cl.
  CPC .............. *A61B 5/1126* (2013.01); *A61B 34/20* (2016.02); *A61F 2/4684* (2013.01); *A61F 2002/4666* (2013.01)

(56) References Cited

U.S. PATENT DOCUMENTS

| | | | |
|---|---|---|---|
| 8,814,877 B2 | 8/2014 | Wasielewski | |
| 8,979,758 B2 | 3/2015 | Stein et al. | |
| 9,247,998 B2 | 2/2016 | Hladio et al. | |
| 9,351,782 B2 | 5/2016 | Stein et al. | |
| 9,408,557 B2 | 8/2016 | Stein et al. | |
| 9,492,290 B2 | 11/2016 | Claypool et al. | |
| 2003/0069644 A1 | 4/2003 | Kovacevic | |
| 2005/0113932 A1* | 5/2005 | Kovacevic | A61F 2/389 623/20.32 |
| 2006/0276849 A1 | 12/2006 | Carlson et al. | |
| 2008/0065225 A1 | 3/2008 | Wasielewski | |
| 2010/0100011 A1* | 4/2010 | Roche | A61B 5/103 600/587 |
| 2010/0249533 A1 | 9/2010 | Pierce et al. | |
| 2011/0319755 A1 | 12/2011 | Stein | |
| 2013/0079671 A1* | 3/2013 | Stein | A61B 5/6878 600/587 |
| 2014/0135773 A1 | 5/2014 | Stein et al. | |

FOREIGN PATENT DOCUMENTS

| | | |
|---|---|---|
| CN | 101583305 | 11/2009 |
| WO | 2011/106861 A1 | 9/2011 |

OTHER PUBLICATIONS

Office Action, dated Aug. 25, 2016, received in connection with CN Patent Application No. 201380076520.4. (English Translation).

International Preliminary Report on Patentability and Written Opinion, dated Sep. 22, 2015, received in connection with International Patent Application No. PCT/US2013/068054.

Office Action and Search Report, dated Aug. 25, 2016, received in connection with CN Patent Application No. 201380076520.4. (and English Translation).

* cited by examiner

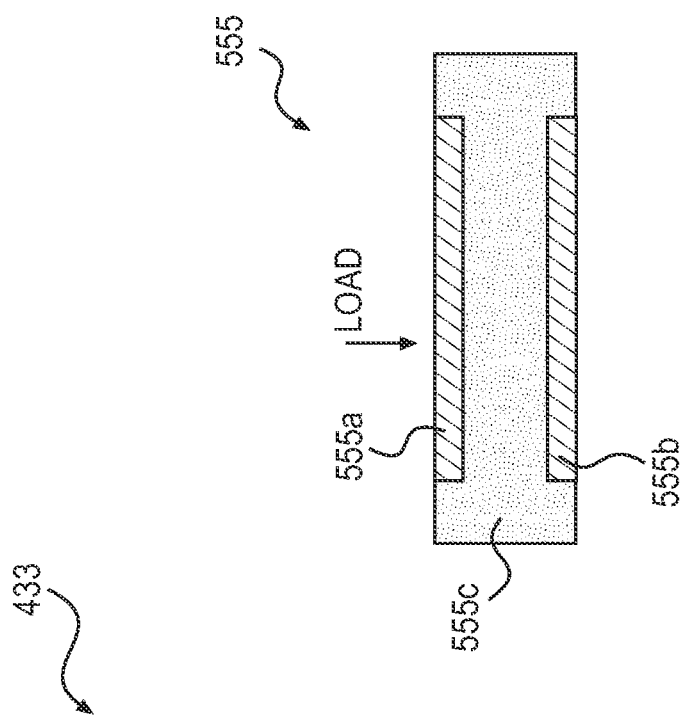
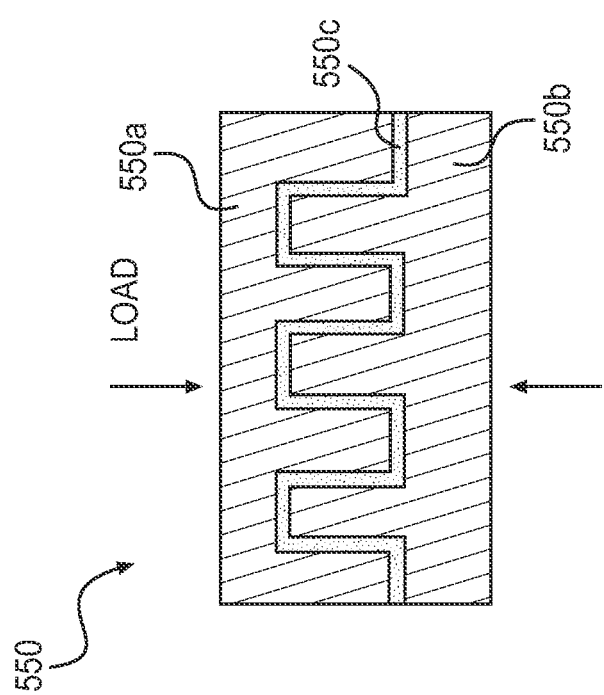

SYSTEMS AND METHODS FOR MEASURING PERFORMANCE PARAMETERS RELATED TO ORTHOPEDIC ARTHROPLASTY

CROSS-REFERENCE TO RELATED APPLICATION

This application is a continuation of application Ser. No. PCT/US2013/068054, filed Nov. 1, 2013, which claims the benefit of U.S. Provisional Application No. 61/803,665, filed Mar. 20, 2013, both of which are incorporated herein by reference in their entireties.

TECHNICAL FIELD

The present disclosure relates generally to orthopedic surgery and, more particularly, to systems and methods for measuring performance parameters associated with joint replacement surgeries.

BACKGROUND

For most surgical procedures, it is advantageous for a surgeon to compare intra-operative progress and post-operative results with a pre-operative plan to ensure that surgical objectives are met. In some surgical procedures, particularly those involving orthopedic arthroplasty, relatively small deviations from a pre-operative plan can translate into significant differences in the functionality of the patient's anatomy. For example, in joint replacement surgery on the knee or hip, small changes in the positioning of the prosthetic joint components may result in considerable differences in the patient's posture, gait, and/or range of motion.

In the early years of joint replacement surgery, intra-operative evaluation of the reconstructed joint was highly subjective. The evaluation process typically involved the surgeon manual placing the leg in different poses and repeatedly articulating the joint through varying degrees of flexion and extension of the leg, while testing the range of motion and relative stability of the joint based on "look and feel." This process for intra-operative evaluation was extremely subjective, and the performance of the reconstructed joint was highly dependent on the experience level of the surgeon. Perhaps not surprisingly, it was difficult for patients and doctors to reliably predict the relative success of the surgery (and the need for subsequent corrective/adjustment surgeries) until well after the initial procedure. Such uncertainty has a negative impact on the ability to predict and control costs associated with surgery, recovery, and rehabilitation.

As orthopedic surgeons and researchers became more familiar with the kinematics and/or kinetics of joint function, techniques for intra-operatively measuring specific joint parameters increased the reliability and repeatability of joint reconstruction surgeries. For example, in knee replacement/reconstruction procedures, surgeons have long sought to ensure that the reconstructed joint is properly "balanced." A poorly-balanced knee can cause undesired condylar separation at the femorotibial interface, instability during flexion and/or extension, and malalignment and/or malrotation, potentially leading to soft tissue damage, improper/excessive implant wear, and general discomfort for the patient. Knee balancing generally refers to the collection of intra-operative processes used by the surgeon to ensure that the reconstructed knee joint restores proper alignment of the leg, appropriate distribution of weight, and stability across a wide range of motion.

There are two conventional techniques for helping orthopedic surgeons balance a knee: gap balancing and measured resection. The gap balancing technique calls for the surgeon to position the femoral component parallel to the resected surface of tibia while the collateral ligaments are equally tensioned. The goal of the gap balancing technique is to maintain a uniform "gap" between the femoral condyles and tibial articular surface for a prescribed uniform tension applied by the collateral ligaments.

The measured resection technique involves resecting the bone based on anatomical landmarks in order to preserve the position of one or more of the anatomical axes associated with the knee joint. To do so, the surgeon makes precision cuts to the bone based on anatomical landmarks of the femur and tibia. During reconstruction of the joint, the surgeon aims to replace the exact thickness of the resected portions to ensure that the reconstructed anatomy (particularly the anatomical axes of rotation) matches the original anatomy of the joint as closely as possible. The theory behind measured resection is that, because everything that is removed is replaced, the original (and ideal) knee balance is restored. One benefit of this technique is that the femur and tibia can be resected independently of one another, so long as the position of the reconstructed axis is maintained.

Regardless of the specific knee balancing technique used, many surgeons rely on measuring devices for independently analyzing/validating certain joint metrics during the procedure. One of the most useful sets of joint metrics includes data indicating the forces present at the tibiofemoral interface. The magnitude and medial-lateral distribution of such forces, for example, can aid the surgeon is determining proper ligament balance and component placement.

Conventional devices for intra-operatively measuring forces use electrical transducers embedded within a joint prosthesis. When the prosthesis is inserted into the joint, compressive forces between the tibia and femur mechanically deform a structural element of the transducer resulting in corresponding change in an electrical output of the transducer. The change in the electrical output is converted by a processor into a force value, which the surgeon uses to make adjustments necessary to balance the knee.

While such conventional devices may accurately measure instantaneous force values in certain situations, such devices may still be inadequate. For example, conventional femorotibial force sensors may be insufficient for measuring the location of medial and lateral forces relative to the corresponding articular surface of the force sensor. Furthermore, many conventional prosthetic force sensors do not include sufficient isolation between the medial and lateral hemispheres of the sensor. As a result, it is difficult for the surgeon to precisely determine the individual forces applied to the medial and lateral articular surfaces.

Additionally, conventional force sensing devices and systems are insufficient in providing the user with ability to combine kinematic and/or kinetic information in order to track the location and magnitude of the medial and lateral forces with respect to joint angles of flexion/extension, varus/valgus, and internal/external rotation. Further, conventional femorotibial force sensing systems do not provide a convenient platform for real-time intra-operative tracking of the movement of the location of the medial and lateral forces as the joint is articulated across the full range of motion. As such, conventional force sensing systems don't provide sufficient capabilities for allowing the surgeon to monitor medial and lateral forces as a function of joint flexion/extension angle and knee alignment.

The presently disclosed systems and methods for intraoperatively tracking joint performance parameters in orthopedic arthroplastic procedures are directed to overcoming one or more of the problems set forth above and/or other problems in the art.

SUMMARY

According to one aspect, the present disclosure is directed to a computer-implemented method for tracking parameters associated with an orthopedic articular joint, the method comprising receiving, at a processor associated with a computer, first information indicative of a force detected at an articular interface between a first bone and a second bone of a patient and receiving, at the processor, second information indicative of an orientation of at least one of the first bone and the second bone. The method may also comprise estimating, by the processor, a location of a center of the force relative to a surface of the articular interface, the estimated location based, at least in part, on the first information. The method may further comprise estimating, by the processor, an orientation angle associated with at least one of the first bone and the second bone relative to a reference axis, the orientation angle, based, at least in part, on the second information. The processor may provide third information indicative of at least one of: the estimated location of the center of the force relative to the surface of the articular interface or the orientation angle associated with the at least one of the first bone and the second bone relative to the reference axis.

In accordance with another aspect, the present disclosure is directed to a force sensing module for measuring kinematic and/or kinetic parameters associated with an orthopedic articular joint. The force sensing module may comprise a housing including an articular surface having a medial portion and a lateral portion, each of which is substantially mechanically isolated from the other. The force sensing module may also include a first set of sensors disposed within the housing, the first set of sensors being mechanically coupled to the medial portion of the articular surface and configured to detect information indicative of a first force incident upon the medial portion of the articular surface. The force sensing module may also include a second set of sensors disposed within the housing, the second set of sensors being mechanically coupled to the lateral portion of the articular surface and configured to detect information indicative of a second force incident upon a lateral portion of the articular surface.

According to another aspect, the present disclosure is directed to a knee balancing system for tracking kinematic and/or kinetic parameters associated with an orthopedic articular joint that comprises an interface between a first bone and a second bone. The knee balancing system comprises a force sensing module, at least a portion of which is configured for implantation within orthopedic articular joint. The force sensing module may be configured to detect information indicative of at least one force incident upon at least a portion of an articular surface of the force sensing module. The knee balancing system may also comprise at least one inertial measurement unit for tracking 3-dimensional joint angles associated with an orthopedic articular joint. The inertial measurement unit is configured to detect information indicative of a 3-dimensional orientation of at least one of a first bone and a second bone. The knee balancing system may further comprise a processing device, communicatively coupled to the force sensing module and at least one inertial measurement unit. The processing device may be configured to estimate a location of at least one force relative to the articular surface, the estimated location based, at least in part, on the information indicative of the force incident upon at least a portion of the articular surface of the force sensing module. The processing device may also be configured to estimate an orientation angle associated with the at least one of the first bone and the second bone relative to a reference axis, the orientation angle, based, at least in part, on the information indicative of the orientation of at least one of the first bone and the second bone. The processing device may be further configured to provide information indicative of at least one of: the estimated location of the force relative to the surface of the articular interface or the orientation angle associated with at least one of the first bone and the second bone relative to the reference axis.

In accordance with another aspect, the present disclosure is directed to a force sensing module for measuring kinematic and/or kinetic parameters associated with an orthopedic articular joint. The force sensing module may comprise a housing including an articular surface and a plurality of sensors disposed within the housing. The plurality of sensors may be mechanically coupled to the articular surface and configured to detect information indicative of a force incident upon the articular surface of the housing. The force sensing module may also include a processing device, communicatively coupled to the each of the plurality of sensors and configured to receive the information indicative of the force incident upon the articular surface of the housing. The processing device may also be configured to estimate a location of a center of the force relative to a boundary associated with the articular surface, and estimate a magnitude of the force at the estimated location of the center of the force.

BRIEF DESCRIPTION OF THE DRAWINGS

FIG. 5B provides a schematic view of an exemplary capacitor-type force detecting transducer that may be implemented within the force sensing insert, in accordance with certain disclosed embodiments;

FIG. 5C provides a schematic view of another exemplary capacitor-type design of a force detecting transducer that may be implemented within the force sensing insert, consistent with certain disclosed embodiments;

DETAILED DESCRIPTION

Figure 1:
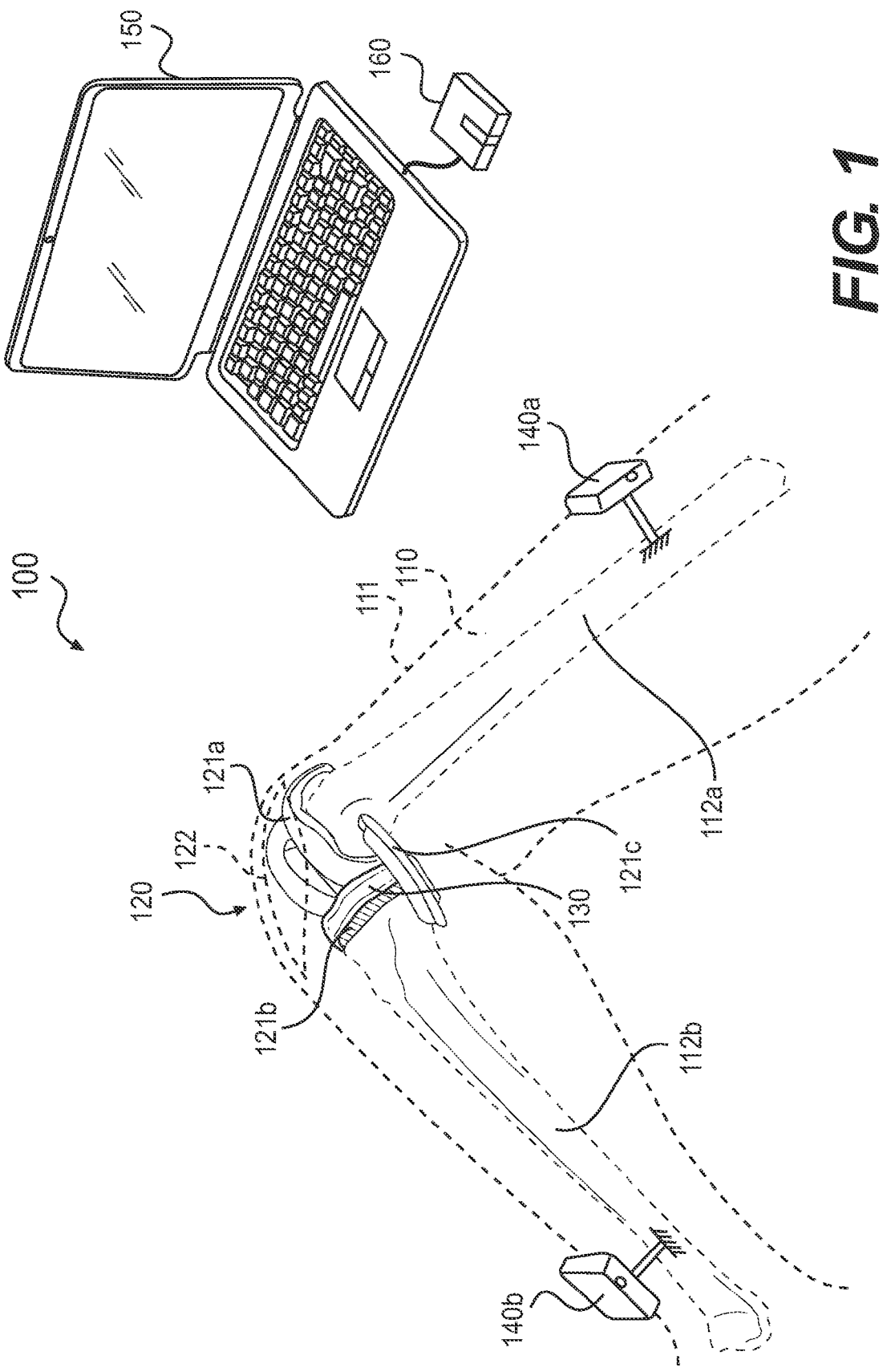
FIG. 1 provides a diagrammatic view of an exemplary knee kinematics and/or kinetics monitoring system (embodied as an intra-operative knee balancing system) consistent with certain disclosed embodiments.

FIG. 1 provides a diagrammatic illustration of an exemplary knee balancing system 100 for intra-operative detection, monitoring, and tracking of kinematic and/or kinetic parameters of an orthopedic joint, such as knee joint 120 of leg 110. For example, in accordance with the exemplary embodiment illustrated in FIG. 1, knee balancing system 100 may embody a system for intra-operatively—and in real-time or near real-time —gathering, analyzing, and tracking performance parameters at knee joint 120 during a full or partial knee replacement procedure. Joint performance parameters may include or embody any parameter for characterizing the behavior or performance of an orthopedic joint. Non-limiting examples of joint performance parameters include any information indicative of force, pressure, angle of flexion and/or extension, torque, varus/valgus displacement, location of center of force, axis of rotation, relative rotation of tibia and femur, tibial component rotation, range of motion, or orientation. Knee balancing system 100 may be configured to monitor one or more of these exemplary kinematic and/or kinetic parameters, track the kinematic and/or kinetic parameters over time (and/or range of motion of the joint), and display the monitored and/or tracked data to a surgeon or medical professional in real-time. As such, knee balancing system 100 provides a platform that facilitates real-time intra-operative evaluation of several joint performance parameters simultaneously.

As illustrated in FIG. 1, knee balancing system 100 may include a force sensing module 130, one or more inertial measurement units 140a, 140b, a processing device (such as processing system 150 (or other computer device for processing data received by force sensing module 130)), and one or more wireless communication transceivers 160 for communicating with one or more of force sensing module 130 or one or more inertial measurement units 140a, 140b. The components of knee balancing system 100 described above are exemplary only, and are not intended to be limiting. Indeed, it is contemplated that additional and/or different components may be included as part of knee balancing system 100 without departing from the scope of the present disclosure. For example, although wireless communication transceiver 160 is illustrated as being a stand-alone device, it may be integrated within one or more other components, such as processing system 150. Thus, the configuration and arrangement of components of force sensing system 100 illustrated in FIG. 1 are intended to be exemplary only. Individual components of exemplary embodiments of force sensing system 100 will now be described in more detail.

Processing system 150 may include or embody any suitable microprocessor-based device configured to process and/or analyze information indicative of performance of the articular joint. According to one embodiment, processing system 150 may be a general purpose computer programmed for receiving, processing, and displaying information indicative of kinematic and/or kinetic parameters associated with the articular joint. According to other embodiments, processing system 150 may be a special-purpose computer, specifically designed to communicate with, and process information for, other components associated with knee balancing system 100. Individual components of, and processes/methods performed by, processing system 150 will be discussed in more detail below.

Processing system 150 may be communicatively coupled to one or more of force sensing module 130 and inertial measurement units 140a, 140b and configured to receive, process, and/or analyze data monitored by force sensing module 130 and/or inertial measurement units 140a, 140b. According to one embodiment, processing system 150 may be wirelessly coupled to each of force sensing module 130 and inertial measurement units 140*a*, 140*b* via wireless communication transceiver(s) 160 operating any suitable protocol for supporting wireless (e.g., wireless USB, Zig-Bee, Bluetooth, Wi-Fi, etc.) In accordance with another embodiment, processing system 150 may be wirelessly coupled to one of force sensing module 130 or inertial measurement unit(s) 140*a*, 140*b*, which, in turn, may be configured to collect data from the other constituent sensors and deliver it to processing system 150.

Wireless communication transceiver(s) 160 may include any suitable device for supporting wireless communication between one or more components of knee balancing system 100. As explained above, wireless communication transceiver(s) 160 may be configured for operation according to any number of suitable protocols for supporting wireless, such as, for example, wireless USB, ZigBee, Bluetooth, Wi-Fi, or any other suitable wireless communication protocol or standard. According to one embodiment, wireless communication transceiver 160 may embody a standalone communication module, separate from processing system 150. As such, wireless communication transceiver 160 may be electrically coupled to processing system 150 via USB or other data communication link and configured to deliver data received therein to processing system 150 for further processing/analysis. According to other embodiments, wireless communication transceiver 160 may embody an integrated wireless transceiver chipset, such as the Bluetooth, Wi-Fi, NFC, or 802.11x wireless chipset included as part of processing system 150.

Force sensing module 130 may include a plurality of components that are collectively adapted for implantation within at least a portion of an articular joint and configured to detect various static and dynamic forces present at, on, and/or within the articular joint. According to one embodiment (and as shown in FIG. 1), force sensing module 130 may embody a trial tibial implant prosthetic component configured for insertion within a partially or fully resected and partially or fully reconstructed knee joint 120. As will be explained in greater detail below, force sensing module 130 may be temporarily removably coupled to a tibial base component 121*b* that is fitted to a resected portion of tibia 112*b* via incision 122 through skin 111 of a patient's leg 110 during a knee replacement procedure. Force sensing module 130 is contoured to articulate with medial and lateral condyles of the femoral prosthetic component 121*b* attached to a resected portion of the patient's femur 112*a*. Force sensing module 130 may also be contoured to articulate with the un-resected natural knee of the patient. Once knee joint 120 is fully or partially reconstructed, force sensing module 130 may be configured to detect various kinematic and kinetic parameters at knee joint 120 in real-time, thereby allowing the surgeon the flexibility to make adjustments to the knee joint (e.g., by balancing the tension of collateral ligaments 121*c*, modifying the position and/or orientation of tibial or femoral prosthetic components 121*a*, 121*b*, or, if necessary, making adjustment to the bone cuts). Exemplary components and subsystems associated with force sensing module 130 will be described in more detail below.

Inertial measurement unit(s) 140*a*, 140*b* may be any system suitable for measuring information that can be used to accurately measure orientation in 3 dimensions. From this orientation information the joint angles such as flexion and/or extension of the orthopedic joint can be derived. Joint flexion (and/or extension) data can be particular useful in evaluating the stability of the joint as the leg is flexed and extended. According to one embodiment, and as illustrated in FIG. 1, two inertial measurement units 140*a*, 140*b* are used and may be attached to the femur and tibia, respectively. Inertial measurements units have their own reference coordinate frames and report their orientation with respect to that frame. Inertial measurement units 140*a*, 140*b* are each configured to measure the relative orientation of a bone with respect to a reference orientation, such as the orientation of the respective sensor when the leg is positioned in a fully extended pose (0 degrees flexion) with no internal/external rotation or varus/valgus forces applied. To improve accuracy of the measurement, an initial calibration of the inertial measurement units with the units lying flat on the patient's table at a known relative orientation may be performed prior to placement on the patient's bones. A calibration fixture or jig that units can be temporarily and removably coupled to in a known relative orientation that can be placed flat on the table surface may be utilized for this calibration. Alternatively or additionally, the inertial measurement units can be registered to anatomic axes of the femur and tibia using alignment guides/jigs and or using kinematic methods known in the art. It should be noted that inertial measurement units 140*a*, 140*b* can be attached to any feature of the patient's anatomy that will provide information indicative of the flexion (and/or extension) of the joint. For example, although FIG. 1 illustrates inertial measurement units 140*a*, 140*b* as attached directly to femur 112*a* and tibia 112*b*, it is contemplated that additional reference attachments may be used. Indeed, according to one exemplary embodiment, one inertial measurement unit may be embedded within force sensing module 130 (which is affixed to the tibia via attachment to tibial prosthetic plate 121*b*) and one inertial measurement unit may be placed in a trial femoral prosthetic component 121*a* (which is affixed to the femur). By affixing each inertial measurement unit(s) 140*a*, 140*b* to different objects, measurement of the orientation of each object can be performed/obtained independently of the orientation or position of the other.

As illustrated in FIG. 1, the inertial measurement unit(s) 140*a*, 140*b* can be fixed on the bones using pins, straps or any such means that can achieves a stable attachment. The actual location of the sensing module relative to the bone is not critical. From the orientation information obtained from inertial measurement unit(s) 140*a*, 140*b*, the tibiofemoral flexion-extension, varus-valgus and rotation angles can be computed. The range of these angles that the knee can traverse is collectively referred to as knee range-of-motion (ROM). Exemplary components and subsystems associated with force sensing module 130 will be described in more detail with respect to FIG. 2.

Figure 2:
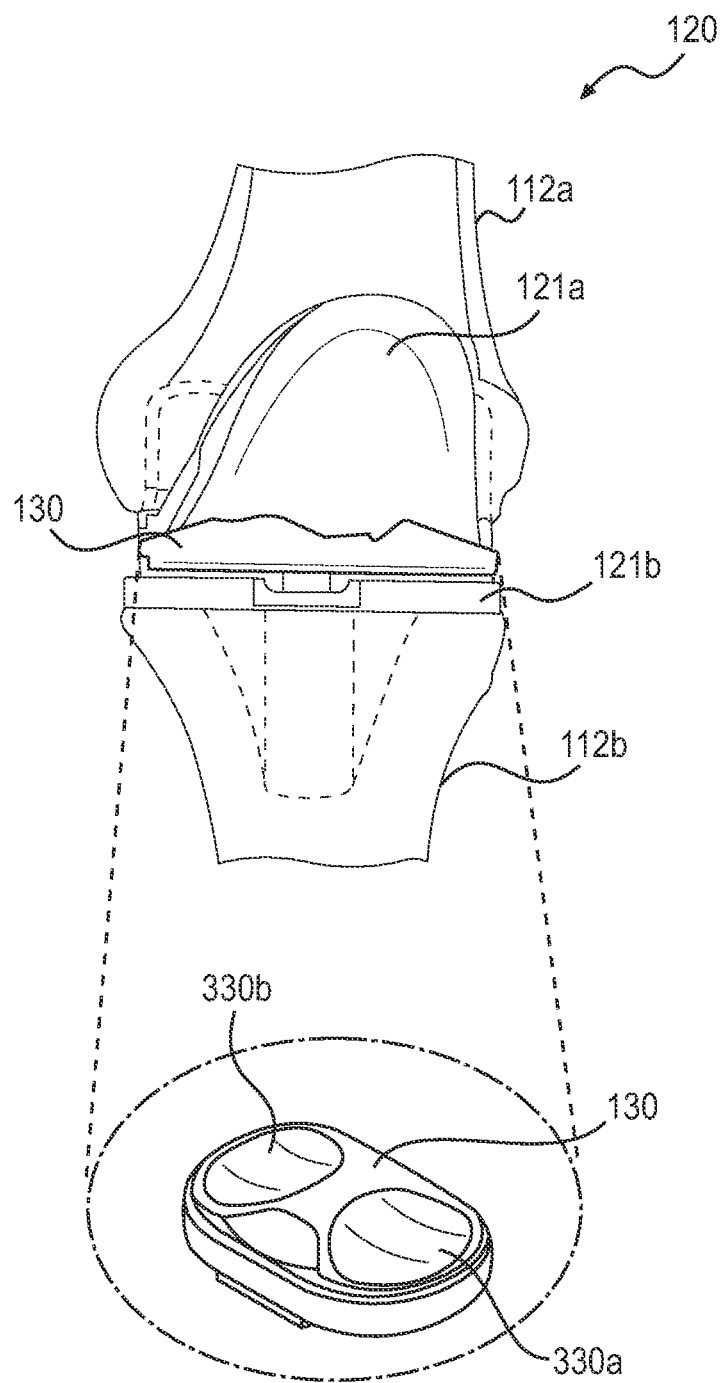
FIG. 2 illustrates a magnified view of an exemplary reconstructed knee joint with a trial force sensing tibial insert, in accordance with certain disclosed embodiments.

FIG. 2 provides a magnified view of knee joint 120 showing force sensing module 130 coupled to tibial prosthetic component 121*b* and configured to articulate with femoral prosthetic component 121*a*. In this embodiment, force sensing module 130 is configured as a trial tibial implant component that is to be used to monitor and evaluate the kinematic and/or kinetic performance of knee joint 120. For example, like a conventional trial tibial insert, an articular surface (i.e., the surface that is configured to articulate with femoral prosthetic component 121*a*) of force sensing module 130 may include a medial portion 330*a* and a lateral portion 330*b* that are contoured to correspond with the contoured shape of medial and lateral condyles of femoral prosthetic component 121*a*. Unlike many conventional knee balancing tools, force sensing module 130 is configured to replicate the shape, size and performance of the tibiofemoral interface with the patella reduced, thereby insuring more accurate kinematic and/or kinetic measurement results and more reliable prediction of post-operative joint performance.

Figure 3:
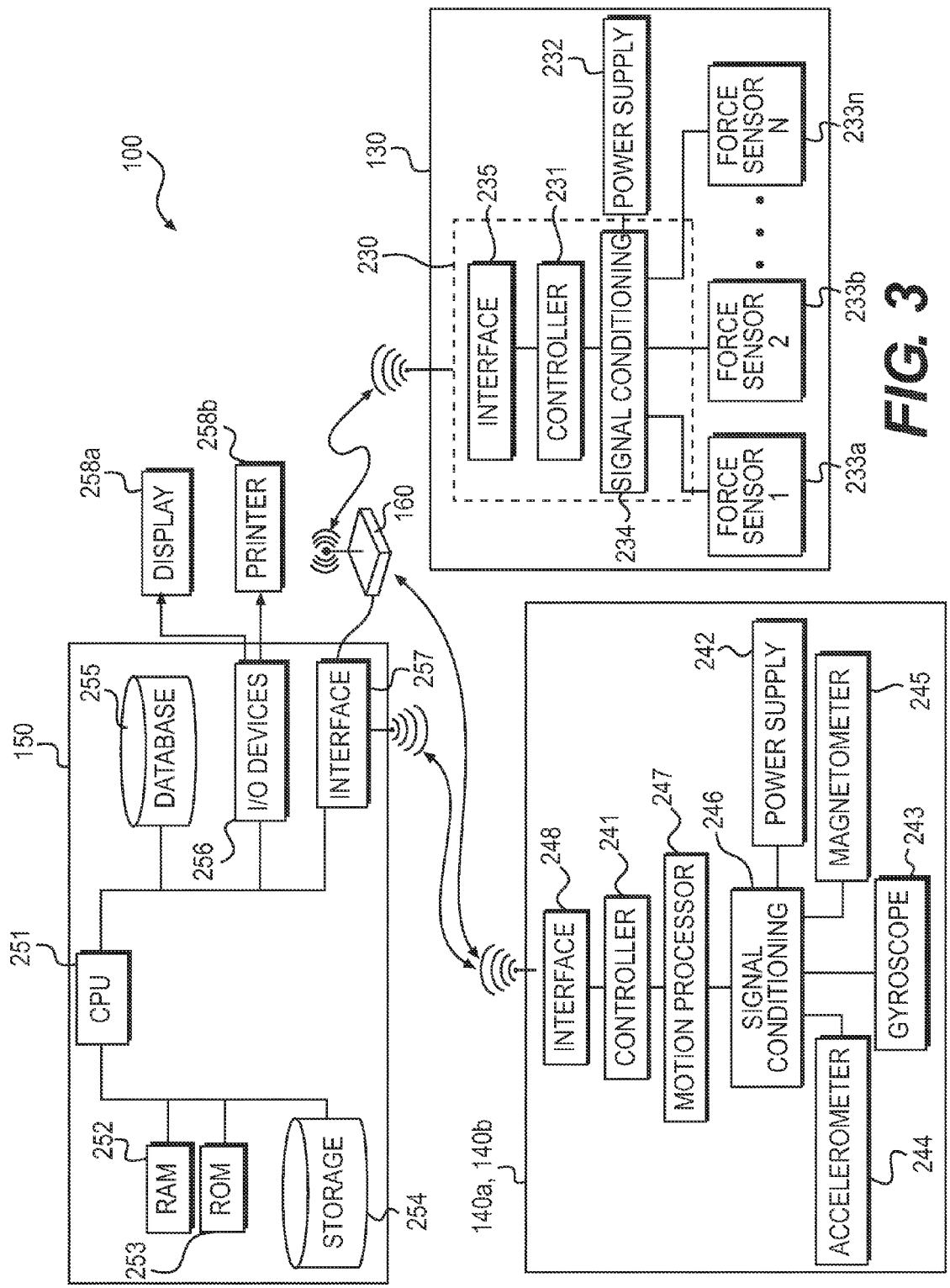
FIG. 3 provides a schematic view of exemplary components associated with a force monitoring system, such as the knee balancing system illustrated in FIG. 1.

FIG. 3 provides a schematic diagram illustrating certain exemplary subsystems associated with force sensing system 100 and its constituent components. Specifically, FIG. 3 is a schematic block diagram depicting exemplary subcomponents of processing system 150, force sensing module 130, and inertial measurement unit(s) 140a, 140b in accordance with certain disclosed embodiments.

As explained, processing system 150 may be any processor-based computing system that is configured to receive kinematic and/or kinetic parameters associated with an orthopedic joint 120, analyze the received parameters to extract data indicative of the performance of orthopedic joint 120, and output the extracted data in real-time or near real-time. Non-limiting examples of processing system 150 include a desktop or notebook computer, a tablet device, a smartphone, or any other suitable processor-based computing system.

For example, as illustrated in FIG. 3, processing system 150 may include one or more hardware and/or software components configured to execute software programs, such as software tracking kinematic and/or kinetic parameters associated with orthopedic joint 120 and displaying information indicative of the kinematic and/or kinetic performance of the joint. According to one embodiment, processing system 150 may include one or more hardware components such as, for example, a central processing unit (CPU) 251, a random access memory (RAM) module 252, a read-only memory (ROM) module 253, a memory or data storage module 254, a database 255, one or more input/output (I/O) devices 256, and an interface 257. Alternatively and/or additionally, processing system 150 may include one or more software media components such as, for example, a computer-readable medium including computer-executable instructions for performing methods consistent with certain disclosed embodiments. It is contemplated that one or more of the hardware components listed above may be implemented using software. For example, storage 254 may include a software partition associated with one or more other hardware components of system 150. Processing system 150 may include additional, fewer, and/or different components than those listed above. It is understood that the components listed above are exemplary only and not intended to be limiting.

CPU 251 may include one or more processors, each configured to execute instructions and process data to perform one or more functions associated with processing system 150. As illustrated in FIG. 3, CPU 251 may be communicatively coupled to RAM 252, ROM 253, storage 254, database 255, I/O devices 256, and interface 257. CPU 251 may be configured to execute sequences of computer program instructions to perform various processes, which will be described in detail below. The computer program instructions may be loaded into RAM 252 for execution by CPU 251.

RAM 252 and ROM 253 may each include one or more devices for storing information associated with an operation of processing system 150 and/or CPU 251. For example, ROM 253 may include a memory device configured to access information associated with processing system 150, including information for identifying, initializing, and monitoring the operation of one or more components and subsystems of processing system 150. RAM 252 may include a memory device for storing data associated with one or more operations of CPU 251. For example, ROM 253 may load instructions into RAM 252 for execution by CPU 251.

Storage 254 may include any type of mass storage device configured to store information that CPU 251 may need to perform processes consistent with the disclosed embodiments. For example, storage 254 may include one or more magnetic and/or optical disk devices, such as hard drives, CD-ROMs, DVD-ROMs, or any other type of mass media device. Alternatively or additionally, storage 254 may include flash memory mass media storage or other semiconductor-based storage medium.

Database 255 may include one or more software and/or hardware components that cooperate to store, organize, sort, filter, and/or arrange data used by processing system 150 and/or CPU 251. For example, database 255 may include historical data such as, for example, stored kinematic and/or kinetic performance data associated with the orthopedic joint. CPU 251 may access the information stored in database 255 to provide a performance comparison between previous joint performance and current (i.e., real-time) performance data. CPU 251 may also analyze current and previous kinematic and/or kinetic parameters to identify trends in historical data (i.e., the forces detected at medial and lateral articular surfaces at various stages of ligament release or bone resection. These trends may then be recorded and analyzed to allow the surgeon or other medical professional to compare the data at various stages of the knee replacement procedure. It is contemplated that database 255 may store additional and/or different information than that listed above.

I/O devices 256 may include one or more components configured to communicate information with a user associated with force sensing system 100. For example, I/O devices may include a console with an integrated keyboard and mouse to allow a user to input parameters associated with processing system 150. I/O devices 256 may also include a display including a graphical user interface (GUI) (such as GUI 900 shown in FIG. 9) for outputting information on a display monitor 258a. I/O devices 256 may also include peripheral devices such as, for example, a printer 258b for printing information associated with processing system 150, a user-accessible disk drive (e.g., a USB port, a floppy, CD-ROM, or DVD-ROM drive, etc.) to allow a user to input data stored on a portable media device, a microphone, a speaker system, or any other suitable type of interface device.

Interface 257 may include one or more components configured to transmit and receive data via a communication network, such as the Internet, a local area network, a workstation peer-to-peer network, a direct link network, a wireless network, or any other suitable communication platform. For example, interface 257 may include one or more modulators, demodulators, multiplexers, demultiplexers, network communication devices, wireless devices, antennas, modems, and any other type of device configured to enable data communication via a communication network. According to one embodiment, interface 257 may be coupled to or include wireless communication devices, such as a module or modules configured to transmit information wirelessly using Wi-Fi or Bluetooth wireless protocols. Alternatively or additionally, interface 257 may be configured for coupling to one or more peripheral communication devices, such as wireless communication transceiver 160.

As explained, inertial measurement unit(s) 140a, 140b may include one or more subcomponents configured to detect and transmit information that either represents a 3-dimensional orientation or can be used to derive an orientation of the inertial measurement unit 140a, 140b (and, by extension, any object rigidly affixed to inertial measurement unit 140a, 140b, such as a tibia and femur of a patient). Inertial measurement unit(s) 140a, 140b may embody a device capable of determining a 3-dimensional orientation associated with any body to which inertial measurement unit(s) 140a, 140b is/are attached. According to one embodiment, inertial measurement unit(s) 140a, 140b may include a controller 241, a power supply 242, and one or more of a gyroscope 243, one or more of an accelerometer 244, or one or more of a magnetometer 245, signal conditioning circuitry 246, and interface 248. Optionally. a temperature sensor may also be included (not shown) to compensate for the effect of temperature on sensor readings.

Although FIG. 3 illustrates inertial measurement unit(s) 140a, 140b as containing 3-axis gyroscope 243, 3-axis accelerometer 244, and 3-axis magnetometer 245, fewer of these devices with fewer axes can be used without departing from the scope of the present disclosure. For example, according to one embodiment, inertial measurement units may include only a gyroscope and an accelerometer, the gyroscope for calculating the orientation based on the rate of rotation of the device, and the accelerometer for measuring earth's gravity and linear motion, the accelerometer providing corrections to the rate of rotation information (based on errors introduced into the gyroscope because of device movements that are not rotational or errors due to biases and drifts). In other words, the accelerometer may be used to correct the orientation information collected by the gyroscope. Similar the magnetometer 245 can be utilized to measure the earth's magnetic field and can be utilized to further correct gyroscope errors. Thus, while all three of gyroscope 243, accelerometer 244, and magnetometer 245 may be used, orientation measurements may be obtained using as few as one of these devices. The use of additional devices increases the resolution and accuracy of the orientation information and, therefore, may be preferable in embodiments where resolution is critical.

Controller 241 may be configured to control and receive conditioned and processed data from one or more of gyroscope 243, accelerometer 244, and magnetometer 245 and transmit the received data to one or more remote receivers. The data may be pre-conditioned via signal conditioning circuitry 246 consisting of amplifiers and analog-to-digital converters or any such circuits. The signals may be further processed by a motion processor 247. Motion processor 247 may be programmed with "motion fusion" algorithms to collect and process data from different sensors to generate error corrected orientation information. Accordingly, controller 241 may be communicatively coupled (e.g., wirelessly via interface 248 as shown in FIG. 3, or using a wireline protocol) to, for example, processing system 150 and configured to transmit the orientation data received from one or more of gyroscope 243, accelerometer 244, and magnetometer 245 to processing system 150, for further analysis. Interface 248 may include one or more components configured to transmit and receive data via a communication network, such as the Internet, a local area network, a workstation peer-to-peer network, a direct link network, a wireless network, or any other suitable communication platform. For example, interface 248 may include one or more modulators, demodulators, multiplexers, demultiplexers, network communication devices, wireless devices, antennas, modems, and any other type of device configured to enable data communication via a communication network. According to one embodiment, interface 248 may be coupled to or include wireless communication devices, such as a module or modules configured to transmit information wirelessly using Wi-Fi or Bluetooth wireless protocols. As illustrated in FIG. 3, inertial measurement unit(s) 140a, 140b may be powered by power supply 242, such as a battery, fuel cell, MEMs micro-generator, or any other suitable compact power supply.

Force sensing module 130 may include a plurality of subcomponents that cooperate to detect force data and, in certain embodiments, joint and/or tibial component orientation information at orthopedic joint 120, and transmit the detected data to processing system 150, for further analysis. According to one exemplary embodiment, force sensing module 130 may include a controller 231, a power supply 232, an interface 235, and one or more force sensors 233a, 233b, . . . , 233n coupled to signal conditioning circuits 234. Those skilled in the art will recognize that the listing of components of force sensing module 130 is exemplary only and not intended to be limiting. Indeed, it is contemplated that force sensing module 130 may include additional and/or different components than those shown in FIG. 3. For example, although FIG. 3 illustrates controller 231, signal conditioning 234, and interface 235 as separate components, it is contemplated that these components may embody one or more modules (either distributed or integrated) within a microprocessor 230. Alternatively or additionally, force sensing module 130 may include one or more integrated inertial measurement units (e.g., motion sensors, orientation sensors, etc.) for determining the orientation of force sensing module 130. Exemplary subcomponents of force sensing module 130 will be described in greater detail below with respect to FIG. 4.

Figure 4:
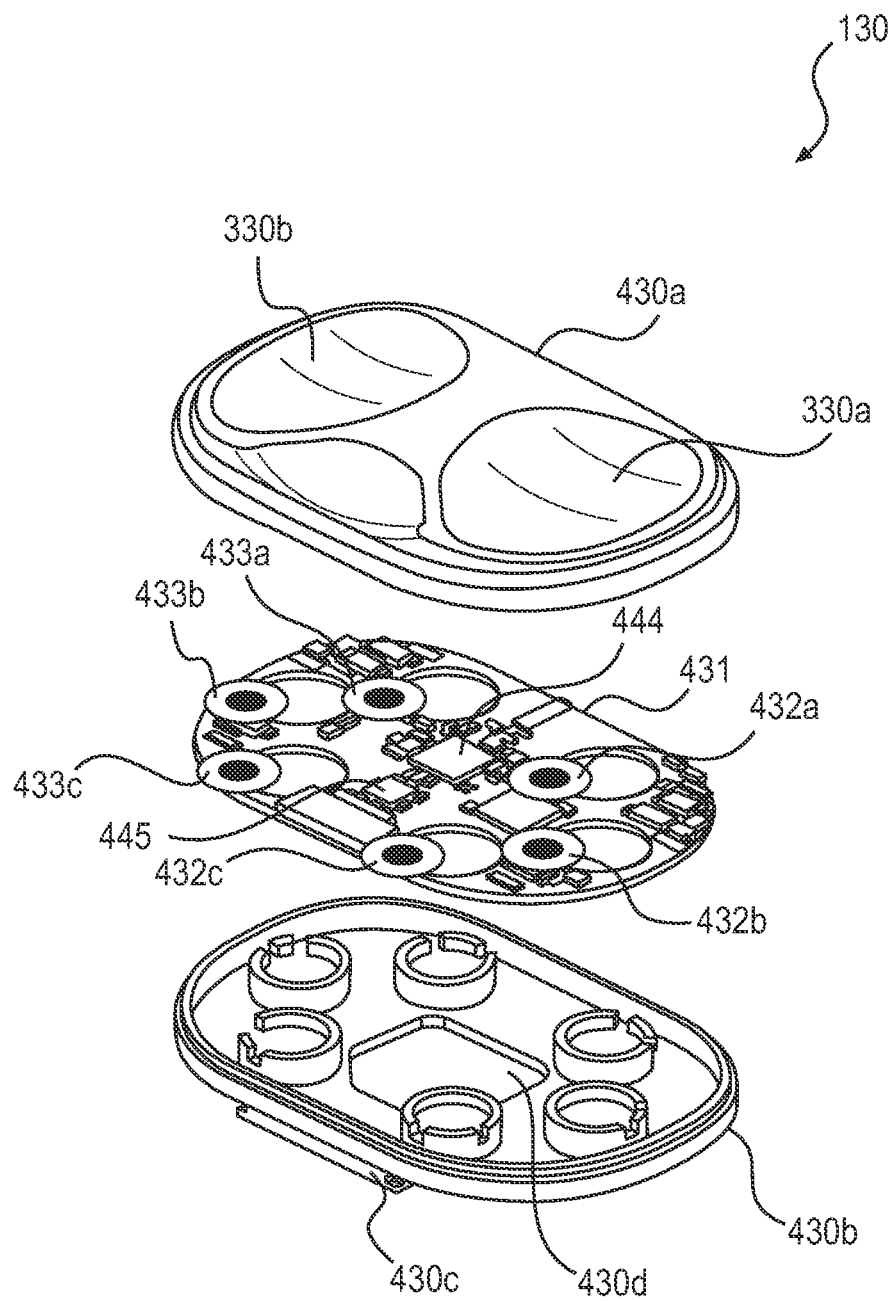
FIG. 4 provides a perspective exploded view of an exemplary trial prosthetic force sensing insert consistent with certain disclosed embodiments.

FIG. 4 illustrates an exploded perspective view of force sensing module 130, consistent with certain disclosed embodiments. As illustrated in FIG. 4, force sensing module 130 may include a housing having an upper portion 430a and a lower portion 430b. As explained, upper portion 430a may comprise an articular surface that includes medial portion 330a and lateral portion 330b, each of which is contoured to interact with respective medial and lateral condyles of a femoral prosthetic component 112a or the condyles of a natural un-resected femur. Lower portion 430b may comprise a bottom surface comprising an interconnect element 430c, configured to removably and slideably couple force sensing module to a metallic tray associated with the tibial prosthetic component 121b. Lower portion 430b of housing may also comprise a tray 430d for receiving and laterally securing a battery (not shown) within housing of force sensing module 130. Upper portion 430a and lower portion 430b may be configured to interlock with one another in order to provide a substantially water-tight containment vessel for the electronic components of force sensing module 130.

Force sensing module 130 may include an electronic circuit board 431, such as printed circuit board (PCB), multi-chip module (MCM), or flex circuit board, configured to provide both integrated, space-efficient electronic packaging and mechanical support for the various electrical components and subsystems of force sensing module 130. Force sensing module 130 may also include controller 231 and interface 234 (shown as microcontroller system-on-chip with integrated RF transceiver 444 in FIG. 4), a first set of force sensors 432a-432c associated with medial portion 330a of force sensing module 130, a second set of force sensors 433a-433c associated with lateral portion 330b of force sensing module 130, a power supply (not shown in FIG. 4, but shown as power supply 232 of FIG. 3), signal conditioning circuitry 234, and (optionally) one or more inertial measurement units 445 for detecting the orientation of force sensing module 130 relative to a reference position.

Microcontroller 444 (and/or controller 231 and interface 235) may be configured to receive data from one or more of force sensors 423a-432c, 433a-433c and inertial measurement unit 445, and transmit the received data to one or more remote receivers. The data may be pre-conditioned via signal conditioning circuitry 246 consisting of amplifiers and analog-to-digital converters or any such circuits. The signal conditioning circuitry may also be used to condition the power supply voltage levels to provide a stable reference voltage for operation of the sensors. Accordingly, microcontroller 444 may include (or otherwise be coupled to) an interface 235 that may consist of a wireless transceiver chipset with or without an external antenna, and may be configured for communicative coupling (e.g., wirelessly as shown in FIG. 3, or using a wireline protocol) to, for example, processing system 150. As such, microcontroller 444 may be configured to transmit the detected force and orientation data received from one or more of sensors 423a-432c, 433a-433c, and inertial measurement unit 445 to processing system 150, for further analysis. Interface 235 may include one or more components configured to transmit and receive data via a communication network, such as the Internet, a local area network, a workstation peer-to-peer network, a direct link network, a wireless network, or any other suitable communication platform. For example, interface 235 may include one or more modulators, demodulators, multiplexers, demultiplexers, network communication devices, wireless devices, antennas, modems, and any other type of device configured to enable data communication via a communication network. According to one embodiment, interface 235 may be coupled to or include wireless communication devices, such as a module or modules configured to transmit information wirelessly using Wi-Fi or Bluetooth wireless protocols. As illustrated in FIG. 3, force sensing module 130 may be powered by power supply 232, such as a battery, fuel cell, MEMs micro-generator, or any other suitable compact power supply.

Force sensing module 130 may optionally include an inertial measurement unit 445 to provide orientation (and/or position) information associated with force sensing module 130 relative to a reference orientation (and/or position). Inertial measurement unit 445 may include one or more subcomponents configured to detect and transmit information that either represents an orientation or can be used to derive an orientation of the inertial measurement unit 445 (and, by extension, any object that is rigidly affixed to inertial measurement unit 445, such as a tibial component which is further attached to the tibia of the patient). Inertial measurement unit 445 may embody a device capable of determining a 3-dimensional orientation associated with any body to which inertial measurement unit 445 is attached. According to one embodiment, inertial measurement unit 445 may include one or more of a gyroscope 243, an accelerometer 244, or a magnetometer 245, signal conditioning circuitry 246, and interface 248.

As illustrated in FIGS. 3 and 4, force sensing module 130 may include a plurality of force sensors, each configured to measure respective force acting on the sensor. The type and number of force sensors provided within force sensing module 130 can vary depending upon the resolution and the desired amount of data. For example, one sensor could be used if the design goal of force sensing system 130 is to simply detect the magnitude of force present at the tibiofemoral interface. If, however, the design goal of force sensing system 130 is to not only provide the magnitude of the forces present at the tibiofemoral interface, but also estimate the location of the center of the applied force, then additional sensors (as few as two, but, preferably, at least three) should be used to provide a sufficient number of data points to allow for accurate planar triangulation of the location of the center of the detected force. Furthermore, in embodiments where the design goal of force sensing system 130 is to provide independent (and simultaneous) monitoring of forces (both magnitude and location of center of force) applied at medial and lateral regions of the articular surface, then force sensing system 130 should include as few as four force sensors (two for each of medial and lateral portions 330a, 330b, respectively), but, preferably, at least six force sensors (three for each of the medial and lateral portions, 330a, 330b, respectively).

As illustrated in FIG. 4, force sensing module 130 may include a first set of force sensors 432a-432c and a second set of force sensors 433a-433c. According to one embodiment, the first set 432a-432c may be mechanically coupled to the underside of medial portion 330a of articular surface of housing 430a. Similarly, the second set 433a-433c may be mechanically coupled to the underside of lateral portion 330b of articular surface of housing 430a. As such, the first set of force sensors 432a-432c may be configured to detect forces incident on medial portion 330a of articular surface, while the second set of force sensor 433a-433c may be configured to detect forces incident on lateral portions 330b of articular surface.

According to certain embodiments consistent with the present disclosure, medial portion 330a and lateral portion 330b are substantially mechanically isolated from one another. As such, forces incident upon medial portion 330a are not meaningfully detectable by a second set of force sensors 433a-433c. Similarly, this substantial mechanical isolation ensures that forces incident upon lateral portion 330b are not meaningfully detectable (e.g., they may appear as noise or interference) by first set of force sensors 432a-432b. It should be noted that substantial mechanical isolation, as the term is used herein, should not be so limited as to require no mechanical interaction between medial portion 330a and lateral portion 330b.

There are multiple ways in which mechanical isolation between medial portions 330a and lateral portions 330b may be achieved. According to one embodiment, the upper portion 430a of housing may embody a three-piece assembly in which medial and lateral portions 330a, 330b are mechanically separate components so as to physically isolate compressive forces on the medial and lateral sides from each other and from the housing side walls and other support structures. In such a configuration, medial portion 330a of articular surface is suspended above force sensors 432a-432c and is free to move by a small but adequate amount relative to the housing in the downward direction when subjected to compressive forces. Similarly, lateral portion 330b of articular surface is suspended above force sensors 433a-433c and is free to move by a small but adequate amount relative to the housing in the downward direction when subjected to compressive forces. The pieces can be securely sealed to the housing with a thin layer of silicone sealant or a gasket of a soft, deformable material like rubber.

According to another embodiment, upper portion 430a of housing may embody a single piece of material in which medial and lateral portions 330a, 300b are constructed to be significantly thinner (and less mechanically resistant to deformation) than the rest of the enclosure, allowing them to flex under compressive loads and transfer the majority of the forces to first and second sets of force sensors 432a-432c, 433a-433c, respectively. In this embodiment, the medialateral bridge separating medial portion 330a and lateral portion 330b, as well as the support structure surrounding the perimeter of upper portion 430a of housing may comprise a substantially thicker and more rigid (and more mechanically resistance to deformation), thereby substantially mechanically isolating medial portion 330a from lateral portion 330b. Exemplary functional subcomponents of force sensors 432a-432c and 433a-433c will now be described in greater detail below with respect to FIGS. 5A-5C.

Force sensors 432a-432c and 433a-433c may be configured using a variety of different resistive or capacitive strain gauges for detecting applied force and/or pressure. Force sensors 432a-432c and 433a-433c each comprise two primary components: a metric portion that has a prescribed mechanical force-to-deflection characteristic and a measuring portion for accurately measuring the deflection of the metric portion and converting this measurement into an electrical output signal (using, for example, strain gauges). Each of FIG. 5A illustrates different designs for the metric portion of the force.

Figure 5A:
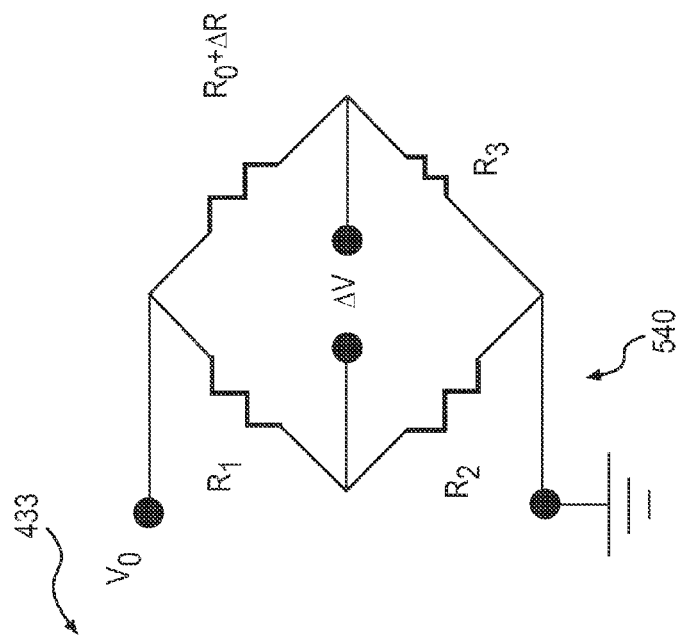
FIG. 5A provides schematic views of exemplary resistive force detecting transducers that may be implemented within the force sensing module, consistent with certain disclosed embodiments.
Figure 5A:
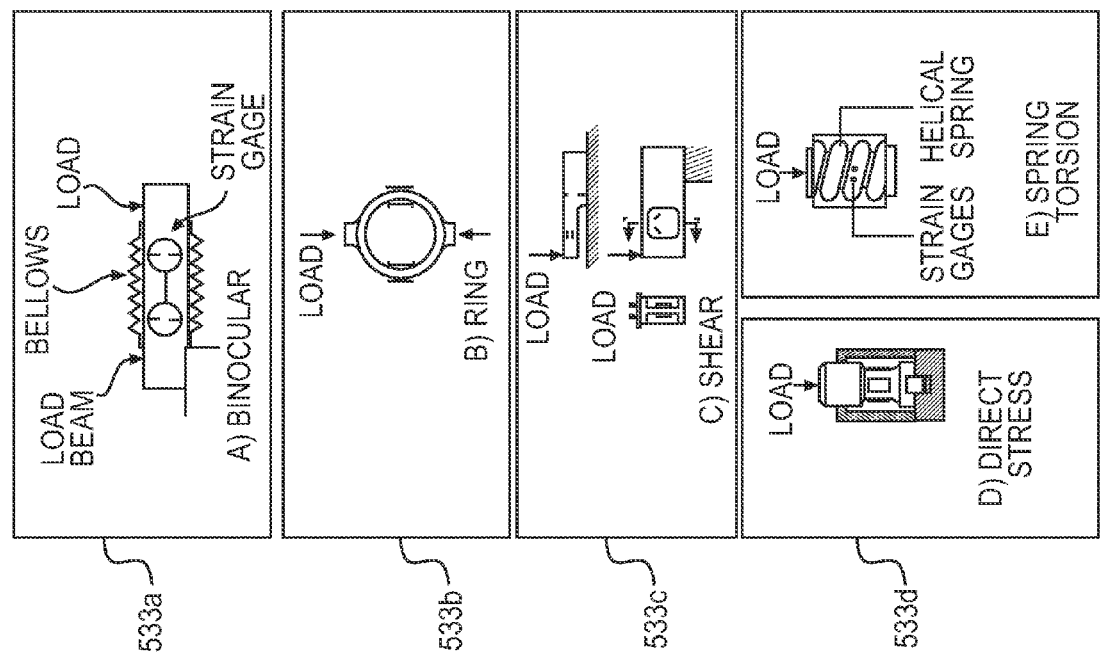

Specifically, FIG. 5A illustrates different designs, each of which is predicated on a different mechanical deformation principle, and any of which may be used in different exemplary embodiments. For example, force sensors 432a-432c and 433a-433c may embody at least one type of the following configurations of force sensors: binocular 533a, ring 533b, shear 533c, or direct stress or spring torsion 533d (including helical, disc, etc.) The strain gauges used with any of the above configurations can be either resistive, piezoresistive, capacitive, optical, magnetic or any such transducers that convert a mechanical deflection and/or strain to a measurable electrical parameter. Alternatively or additionally, any suitable resistive strain gauge, whose output resistance value changes with respect to the application of mechanical force, can be used as force sensors 432a-432c, 433a-433c. In certain embodiments, the resistive strain gauge could be the transducer class S182K series strain gauges from Vishay Precision Group, Wendell N.C. In another embodiment, as shown in FIG. 4, force sensors 432a-432c and 433a-433c are load cells that combine the metric and measuring portion as a single package, such as the LBS miniature compression load button manufactured by Interface of Scottsdale Ariz. or LLB 130 Subminiature Load Button manufactured by Futek of Irvine, Calif. can be used. Such load cells have wired connections that can be directly soldered on to the printed circuit board.

Because the structures used in resistive sensors tend to exhibit relatively small changes in resistance under mechanical stress, a separate electrical circuit that is capable of detecting such small changes may be required. According to one embodiment, a Wheatstone bridge circuit 540 may be used to measure the static or dynamic electrical resistance due to small changes in resistance due to mechanical strain.

As an alternative or in addition to resistive strain gauges, force sensors 432a-432c and 433a-433c may embody capacitive-type strain gauges. Capacitive-type strain gauges, such as those illustrated in the embodiments shown in FIGS. 5B and 5C, typically comprise two metal conductors fashioned as layers or plates separated by a dielectric layer. The dielectric layer may comprise a compressible material, such that when force is applied to one or more of the metal plates the dielectric layer compresses and changes the distance between the metal plates. This change in distance causes a change in the capacitance, which can be electrically measured and converted into a force value.

Exemplary designs of capacitive-type force sensors are illustrated in FIGS. 5B and 5C. For example, FIG. 5B illustrates capacitive-type sensor 550 with a lateral comb configuration (i.e., having a serpentine dielectric channel 550c separating metal plates 550a and 550b). Because this lateral-comb configuration effectively comprises several capacitors (at each of the interlocking comb-teeth), a lateral comb capacitive sensor 550 functions across a relatively large range of forces and exhibits good sensitivity and signal to noise ratio.

According to another exemplary embodiment, capacitive-type force sensor may embody a more conventional parallel-plate capacitor device 555, with metal plates 555a and 555b arranged in parallel around a dielectric layer 555c. Although less sensitive to compressive forces, parallel plate designs are simpler and less expensive to implement, and can be fairly accurate over smaller ranges of compressive forces.

Figure 6:
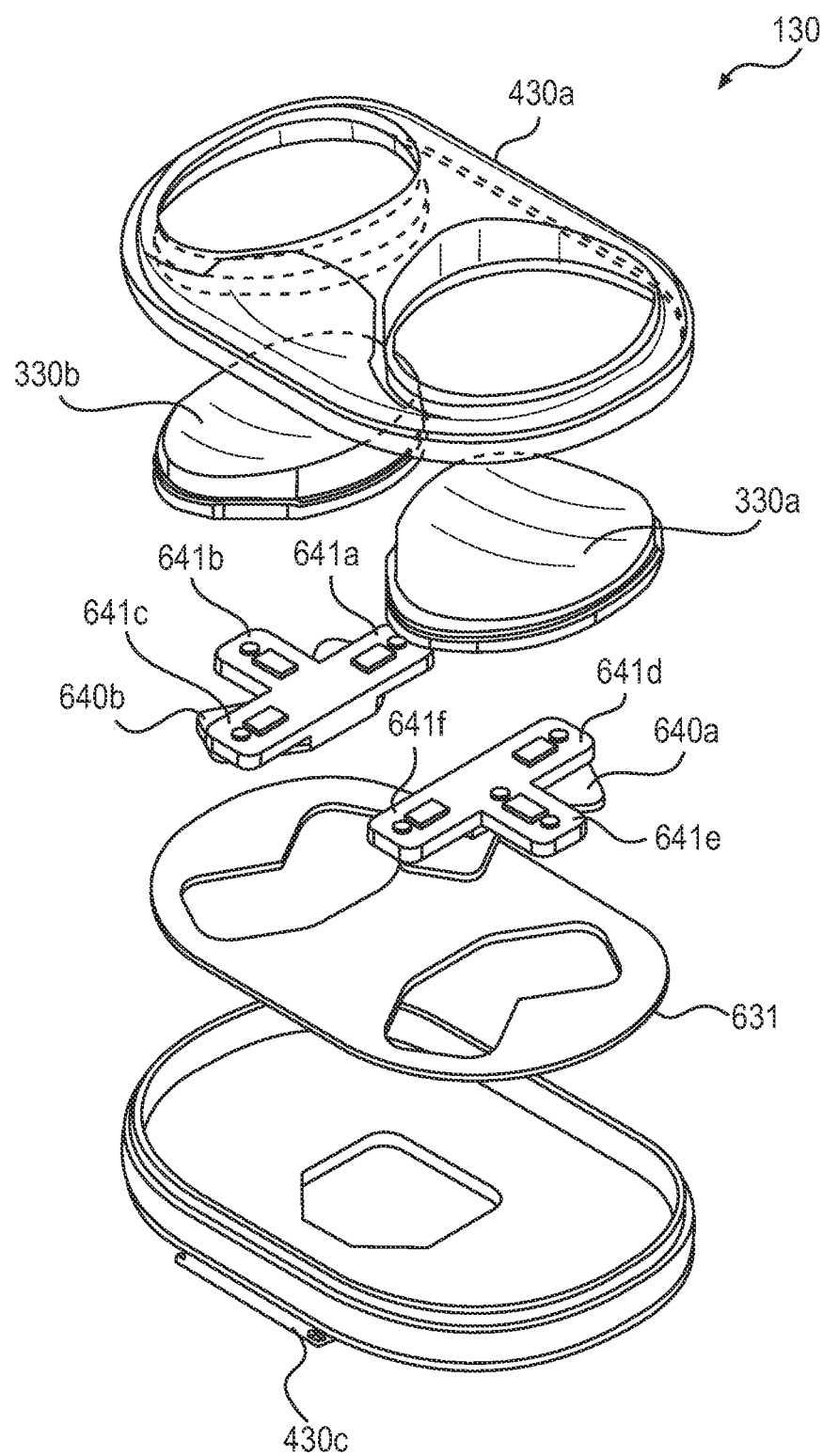
FIG. 6 provides a perspective exploded view of another exemplary trial prosthetic force sensing insert consistent with certain disclosed embodiments.

FIG. 6 provides a perspective exploded view of an alternate design of force sensing module 130. In the embodiment illustrated in FIG. 6, medial portion 330a and lateral portion 330b are not integrated as part of upper portion 430a of the housing. Having physically separate medial and lateral portions 330a, 330b provides better mechanical isolation between medial and lateral portions 330a, 330b, ensuring a greater degree of independence between medial and lateral force measurements.

Force sensing module 130 illustrated in FIG. 6 may comprise a medial force sensing device 640a and a lateral force sensing device 640b. Unlike the embodiment of force sensing device 130 illustrated in FIG. 4, each of medial and lateral force sensing device 640a, 640b of force sensing module 130 of FIG. 6 embodies a single force sensing structure that includes a plurality of transducer elements 641a-641f. Each of transducer elements 641a-641f is configured to independently detect a force value associated with a force incident on a respective location on either the medial portion 330a or the lateral portion 330b of the articular surface of the housing. The configuration of medial and lateral force sensing devices 640a, 640b will be discussed in further detail below with respect to FIGS. 7A-7E.

As with the embodiment of the force sensing module illustrated in FIG. 4, force sensing module 130 of FIG. 6 may include an electronic circuit board 631, the components of which have not been illustrated in detail. Nevertheless, electronic circuit board 631 may comprise a printed circuit board (PCB), multi-chip module (MCM), or flex circuit board, configured to provide both integrated, space-efficient electronic packaging and mechanical support for the various electrical components and subsystems of force sensing module 130. Electronic circuit board 631 may also include a microcontroller (with communication interface module) (not shown in FIG. 6, but similar to that shown in FIG. 4), a power supply (not shown in FIG. 6, but similar to power supply 232 of FIG. 3), signal conditioning circuits (not shown in FIG. 6, but similar to signal conditioning circuit 234 of FIG. 3), and (optionally) one or more inertial measurement units (similar to that disclosed and illustrated with respect to FIG. 4) for detecting the orientation of force sensing module 130 relative to a reference position. Electronic circuit board 631 may also include a plurality of electrical interconnects to connect force sensing devices 640a, 640b and other components to the microcontroller other electronic components of electronic circuit board 631.

Figure 7C:
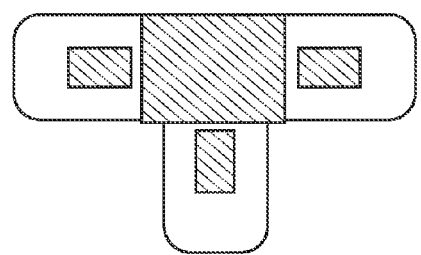
FIG. 7C provides a cross section view (facing bottom to top) of an exemplary force sensing transducer shown in FIG. 6A, in according with certain disclosed embodiments.
Figure 7E:
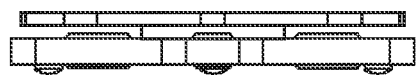
FIG. 7E provides a front view of an exemplary force sensing transducer shown in FIG. 6A, in accordance with certain disclosed embodiments.
Figure 7B:
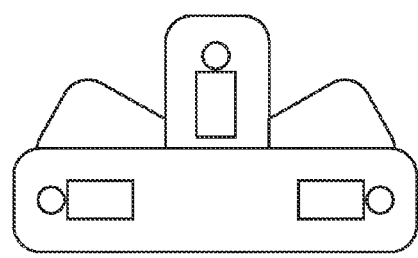
FIG. 7B provides a top view of an exemplary force sensing transducer shown in FIG. 6A, consistent with certain disclosed embodiments.
Figure 7D:
FIG. 7D provides a side view of an exemplary force sensing transducer shown in FIG. 6A, consistent with certain disclosed embodiments.
Figure 7A:
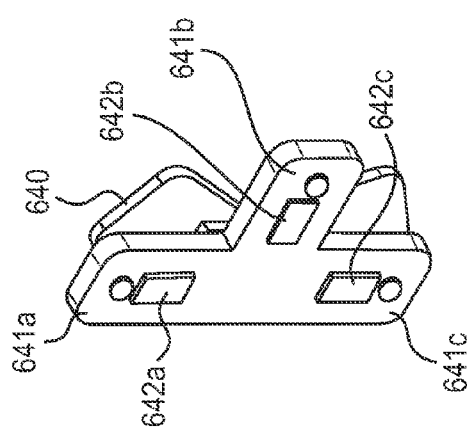
FIG. 7A provides a perspective top view of an exemplary force sensing transducer used in an exemplary trial prosthetic force sensor, in accordance with certain disclosed embodiments.

FIGS. 7A-7E each provide a different view of exemplary force sensing devices 640a, 640b used in the embodiment of force sensing module 130 illustrated in FIG. 6. Specifically, FIG. 7A illustrates a perspective top view, FIG. 7B illustrates and overhead top view, FIG. 7C illustrates a cross section view of the cantilever-type mechanical structure of force sensing devices 640a, 640b, FIG. 7D illustrates a side view of inverted force sensing devices 640a, 640b, and FIG. 7E illustrates a front view.

As shown in FIG. 7A, each of force sensing modules 640a, 640b may include a plurality of transducers (each embodying an individual load sensing element). Each transducer includes a respective cantilever component 641, one or more respective strain gauges 642, and a contact point. At least a portion of the cantilever component 641 is configured to deform in response to the first force incident upon the articular surface. Each cantilever has a well-defined contact point that is configured to interact with a corresponding contact point located on the underside of respective medial or lateral portion 330a, 330b of the articular surface of the housing. According to the exemplary embodiment of FIG. 7A, this contact point may embody a plastic circular nipple (shown in FIG. 7A as the hemispheric structure located toward the distal end of the cantilever structure). This hemispheric structure may be configured to contact a complementary structure located on the underside of a corresponding medial or lateral portion 330a, 330b of articular surface, such that, when a load is applied to the corresponding medial or lateral portion 330a, 330b, the force is mechanically translated onto cantilever beam, forcing the cantilever beam to mechanically deform consistent with the magnitude of the load applied at that particular location of medial or lateral portion 330a, 330b.

As explained, each of transducers of force sensing modules 640a, 640b may also include one or more respective strain gauges 642. Strain gauge 642 may be coupled to a respective cantilever component 641 and configured to measure the deformation in the respective cantilever component. Strain gauge 642 may embody resistive strain gauges, meaning that it exhibits a change in resistance in response to the pressure detected at the corresponding cantilever component 641. According to one embodiment, strain gauges 641 may be the Transducer-Class strain gauges manufactured by Micro-Measurement (Wendell, N.C.).

As illustrated in the embodiment shown in FIGS. 7A-7E, force sensing modules 640a, 640b may include three cantilever elements, extending laterally from a central base support element. Each cantilever component 641 associated with the plurality of transducers is vertically supported at a proximal end by a common central base component. Those skilled in the art will recognize that additional or fewer cantilever components 641 may be included as part of force sensing modules 640a, 640b. Additionally, the base support element may be a single support element shared by sensing module 640a, 640b, and may be large enough to have lateral dimensions roughly equal to the lateral dimensions of the bottom piece of the housing 430b. In the exemplary embodiment illustrated in FIGS. 7A-7E, three cantilever components are used to provide a balance between cost and precision of the force locating capability of force sensing modules 640a, 640b versus load cells provided by vendors as shown in the embodiment of FIG. 4.

Figure 8:
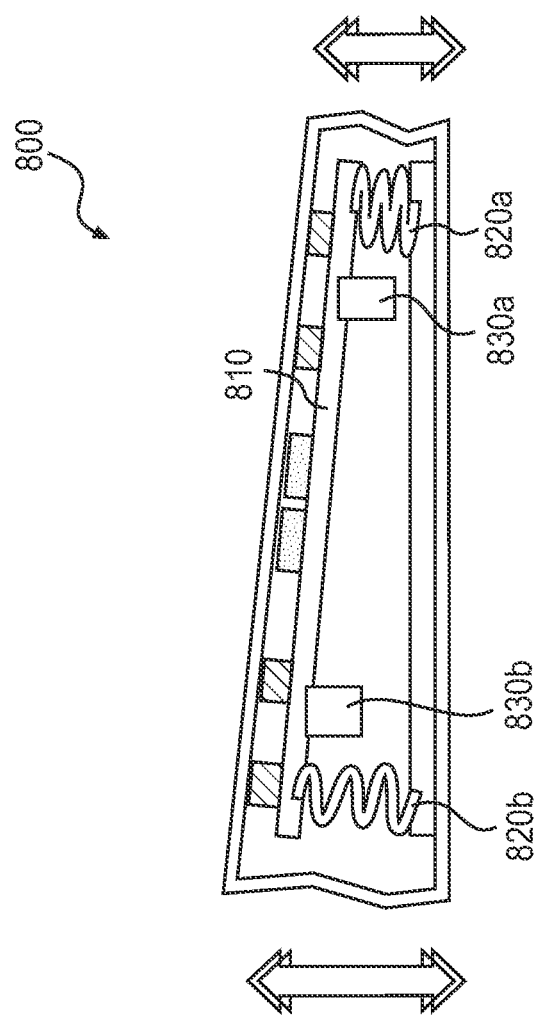
FIG. 8 provides a schematic cross-sectional view of an exemplary gap measurement module, consistent with certain disclosed embodiments.

FIG. 8 illustrates an alternate knee balancing configuration, consistent with the disclosed embodiments. Specifically, FIG. 8 illustrates a gap measurement module 800, that can be used to determine the gap distance between two surfaces located at the joint interface (e.g., as at the interface between the tibia and femur). As illustrated in FIG. 8, gap measurement module 800 may include a plurality of springs (such as medial spring 820a and lateral spring 820b) configured to change length in response to compressive forces at the tibiofemoral interface. In operation, biasing the springs on the medial and lateral sides can change the thickness of the sensing module dynamically.

Various spring designs can be employed such as, for example and without limitation, helical compression springs, constant force springs, cantilever springs, etc. In certain embodiments, a screw can also be employed to enable adjustment in tension and thereby vary the forces experienced by the medial and lateral sides. In a further exemplary aspect, the amount of tension of each spring could be confirmed with measurements made by integrated force sensors similar to embodiments illustrated in FIG. 4 and FIG. 6. One skilled in the art will appreciate that, once the forces are equalized, the gap measurements can be employed to perform "gap balancing", one of the techniques utilized for ligament balance.

In other aspects, a plurality of linear displacement or distance sensors 830a, 830b can also be incorporated in the housing, and can be configured to determine the distance between the top and bottom of the housing dynamically. In this aspect, distance sensors 830a, 830b each comprise a transducer operable to convert linear displacement to an electrical signal that can then be processed and transmitted wirelessly. Such a transducer could be, for example and without limitation, optical, inductive, electromagnetic, resistive or the like. In another aspect, the device disclosed in U.S. Pat. No. 8,026,729 filed on Apr. 1, 2009, hereby incorporated by reference, can be particularly suited.

Gap measurement module 800 may include an electronic circuit board 810 that includes a microcontroller configured to receive data from distance sensors 830a, 830b and wirelessly communicate the received information to an off-board monitoring system, such as processing system 150.

According to one embodiment, gap measurement module 800 may include a plastic or silicon housing with flexible sides to accommodate the change in vertical dimensions. This flexible housing may embody a bellows or accordion type housing or thinner housing walls compared to the housing top and bottom can be used to allow for changes in vertical dimensions.

Figure 9:
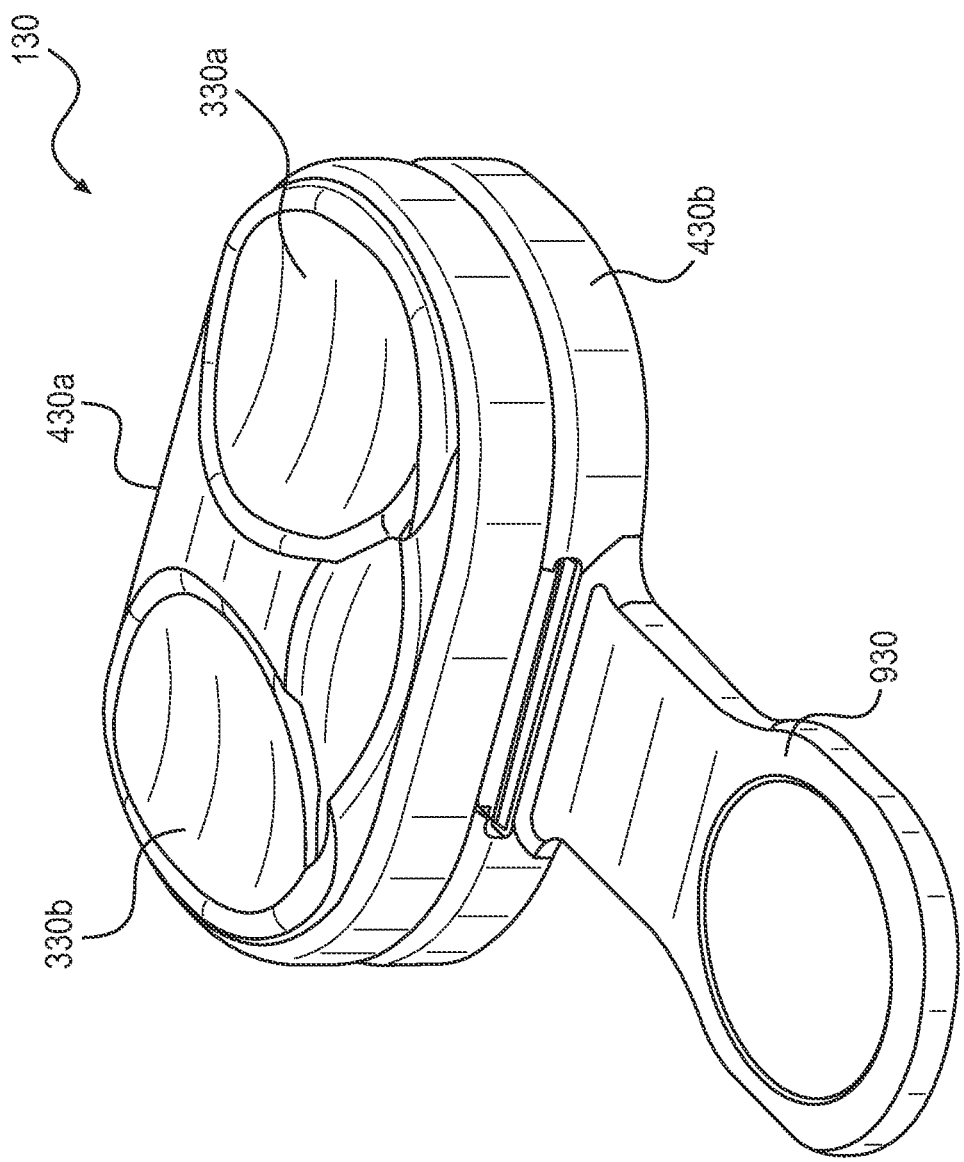
FIG. 9 provides a perspective view of an exemplary trial prosthetic force sensing insert with removable positioning handle, consistent with certain disclosed embodiments.

As explained, force sensing module 130 may be configured to be removably positioned within the articular joint 120 in a variety of ways. For example, force sensing module 130 may be slideably coupled to a tibial prosthetic plate 121b during extended periods of joint evaluation. In some situations, however, it may be impractical to couple force sensing module 130 to the tibial plate. For example, when a surgeon is reasonably certain that additional bone cuts or prosthetic component repositioning may be required, it may be time consuming and inconvenient to have to frequently couple and remove force sensing module 130 to and from tibial prosthetic plate 121b. In such situations, it may be advantageous to have a system for quickly (and temporarily) positioning force sensing module 130 at or within articular joint 120. Another example is when a surgeon has only made a tibial cut and wishes to assess joint performance with an un-resected or partially resected femur. In this situation, there may not be enough room for a tibial prosthetic plate 121b or it not may not be practical and/or useful from a work flow or clinical perspective to utilize a tibial plate. FIG. 9 illustrates one embodiment of an elongated handle member 930 configured to removably position the force sensing module 130 within the orthopedic articular joint 120.

As illustrated in FIG. 9, elongated handle member 930 may include a channel that complimentarily corresponds to slideable connection interface 430a of force sensing module 130. As such, elongated handle member 930 can be slideably coupled to force sensing module 130 and used in situations in which the force sensing module 130 need to be repositioned within the orthopedic joint 120 on a more frequent basis.

Figure 10:
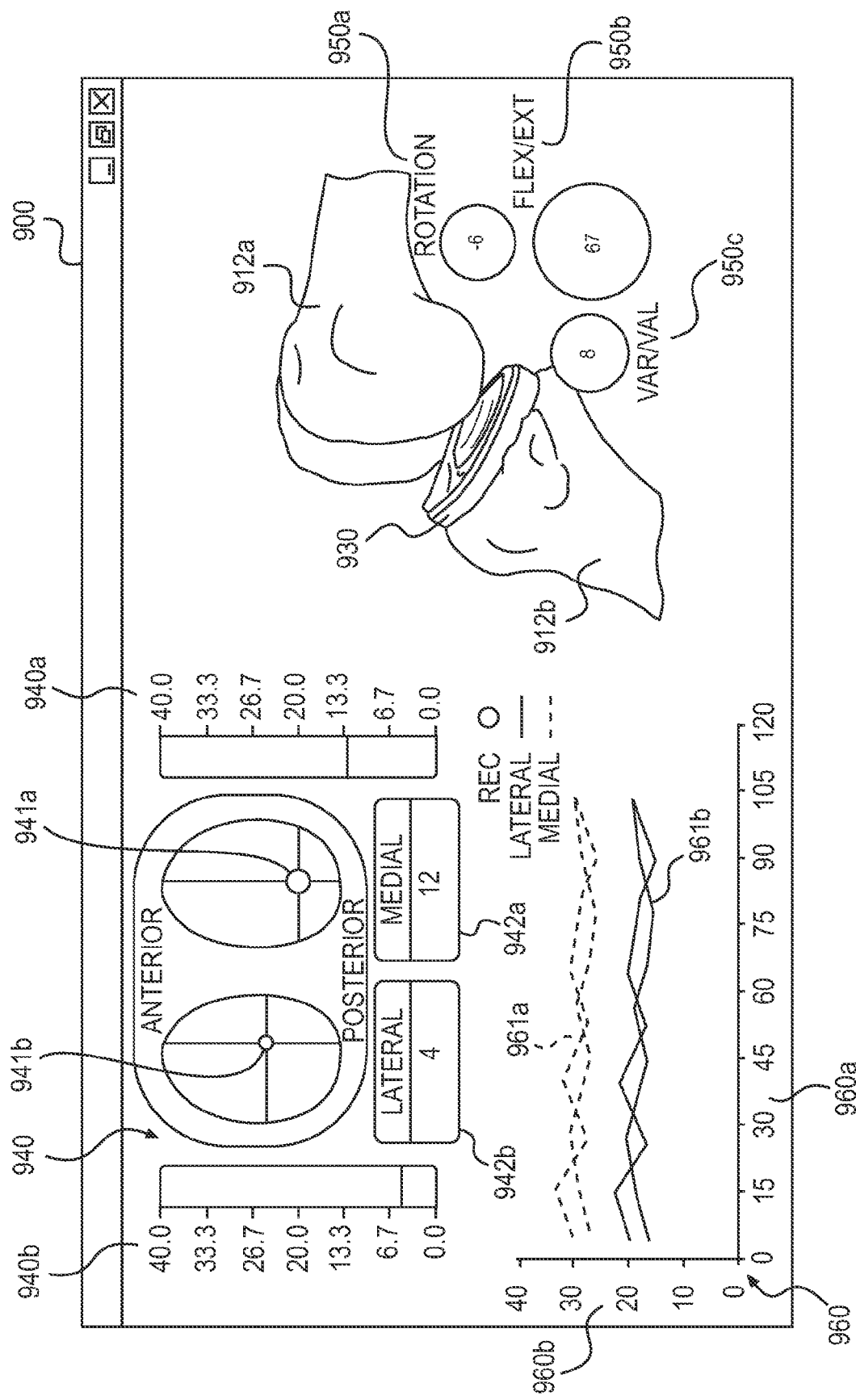
FIG. 10 illustrates an embodiment of a user interface that may be provided on a monitor or output device for intra-operatively displaying the monitored joint performance parameters in real time, in accordance with the disclosed embodiments.
Figure 10A:
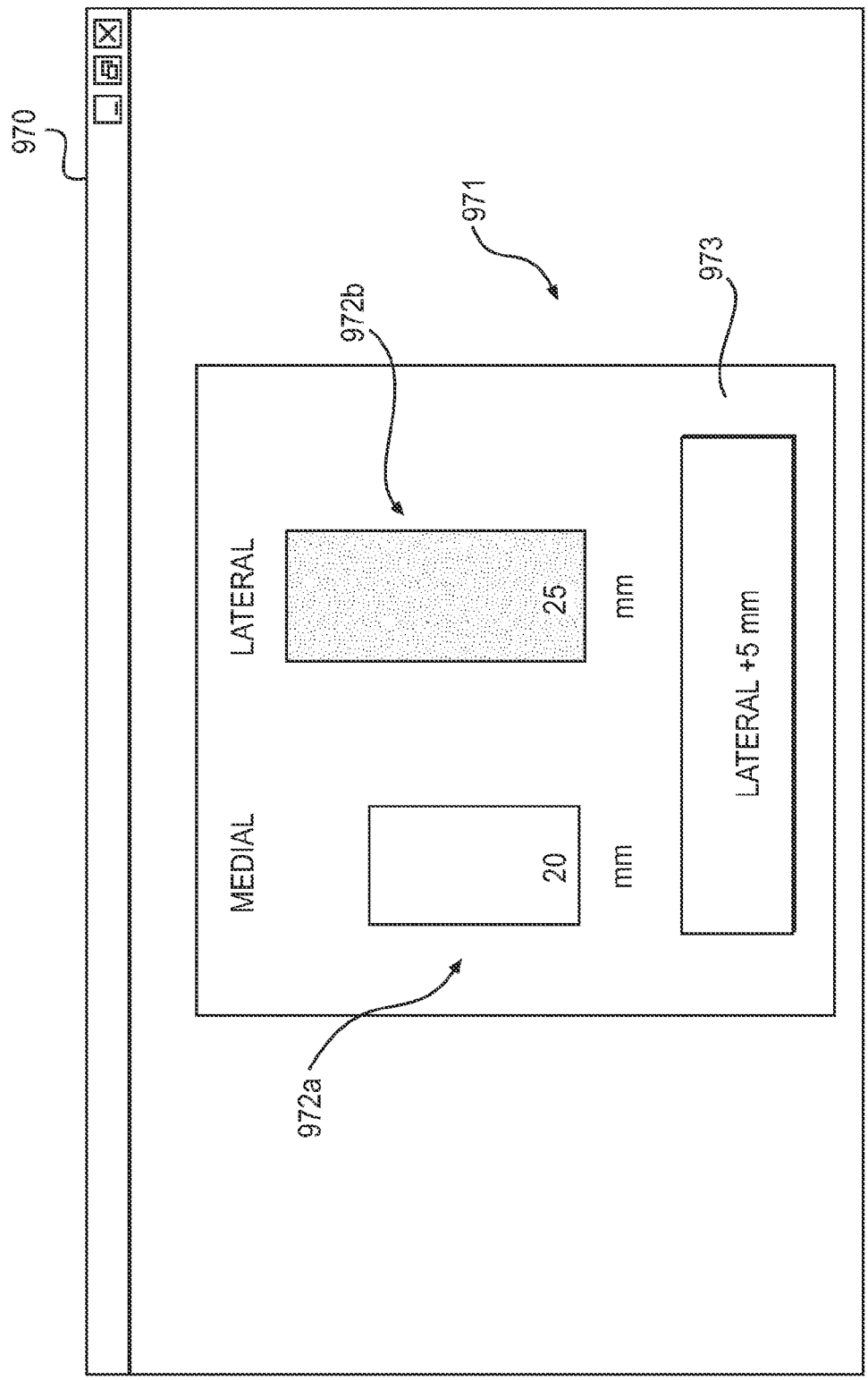
FIG. 10A illustrates an alternate embodiment of a user interface that may be provided on a monitor or output device for intra-operatively displaying the monitored joint performance parameters in real time, in accordance with the disclosed embodiments.
Figure 11:
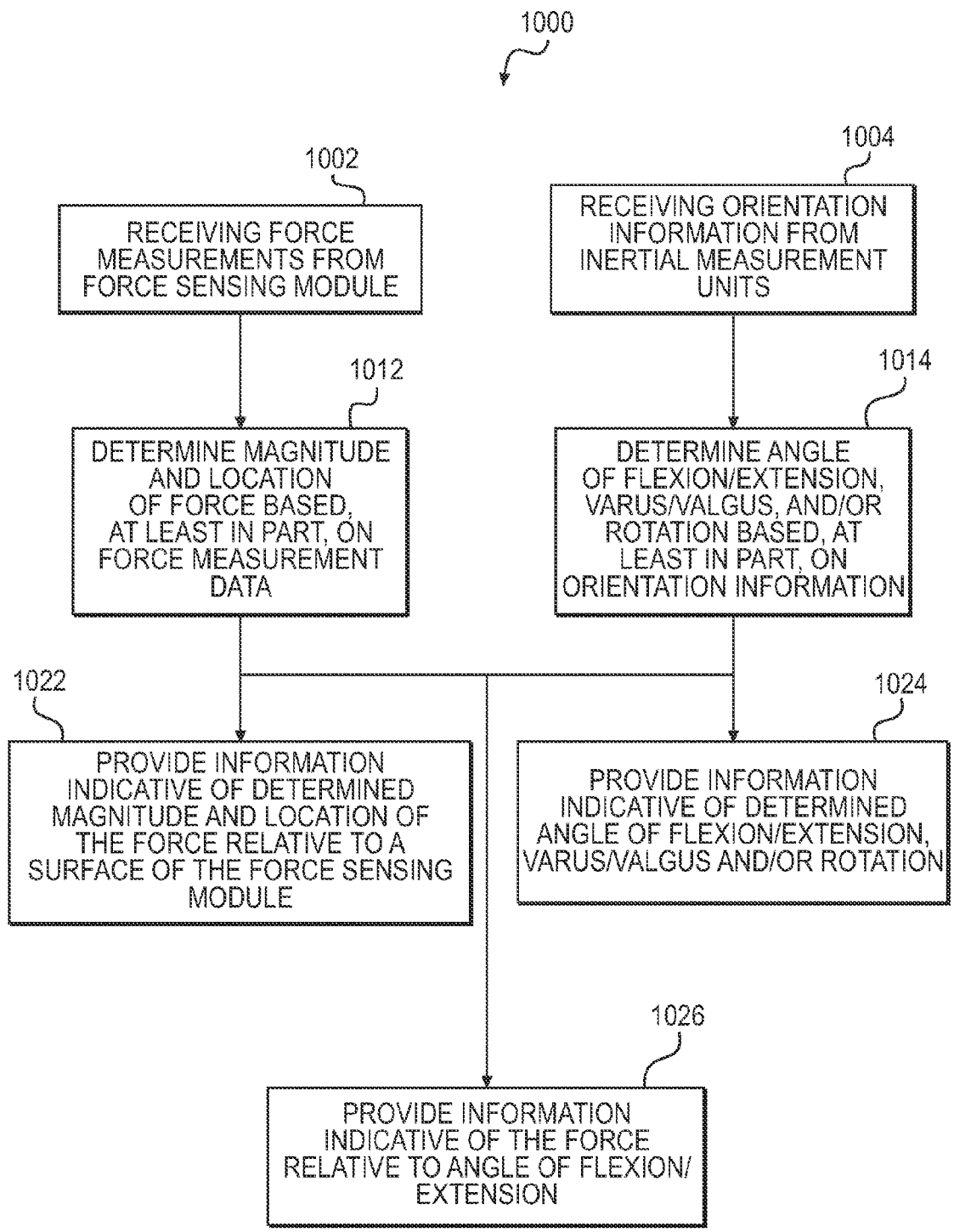
FIG. 11 provides a flowchart depicting an exemplary process to be performed by one or more processing devices associated with force monitoring systems consistent with the disclosed embodiments.

Processes and methods consistent with the disclosed embodiments provide a system for monitoring the forces (or gaps) present at an orthopedic joint 120 and the 3-dimensional alignment and/or angles of the joint, and can be particularly useful in intra-operatively evaluating the kinematic and/or kinetic performance of the joint. As explained, while various components, such as force sensing module 130 and inertial measurement units 140a, 140b can monitor various physical parameters (e.g., magnitude and location of force, orientation, etc.) associated with the bones and interfaces that make up orthopedic joint 130, processing system 150 provides a centralized platform for collecting and compiling the various physical parameters monitored by the individual sensing units of the system, analyzing the collected data, and presenting the collected data in a meaningful way to the surgeon. FIGS. 10, 10A, and 11 illustrate exemplary processes and features associated with how processing system 150 performs the data analysis and presentation functions associated with force sensing system 100.

FIGS. 10 and 10A provide exemplary screen shots 900, 970 corresponding to a graphical user interface (GUI) associated with processing system 150. Screen shot 900 may correspond to embodiments in which force sensing module 130 is configured to detect forces present at orthopedic joint 120. Screen shot 970 may correspond to embodiments in which gap measurement module 800 is configured to detect a gap distance at the tibiofemoral interface. Specific details for each of these screen shots will be described in detail below with respect to the exemplary processes and methods performed by processing system 150, as outlined in FIG. 11.

FIG. 11 provides a flowchart illustrating an exemplary data analysis process 1000 performed by processing system 150. As explained, processing system 150 may include software configured to receive, process, and deliver various kinematic and/or kinetic performance data to other subcomponents and users associated with force sensing system 100.

As illustrated in FIG. 11, the process may commence when processing system 150 receives force measurement information from force sensing module 130 (or gap measurement information from gap measurement module 800) (Step 1002) and/or orientation information from inertial measurement unit(s) 140a, 140b (Step 1004). As explained, processing system 150 may include one or more communication modules for wirelessly communicating data with force sensing module 130 (or gap measurement module 800) and/or inertial measurement unit(s) 140a, 140b. As such, processing system 150 may be configured establish a continuous communication channel with force sensing module 130 and/or inertial measurement unit(s) 140a, 140b and automatically receive kinematic and/or kinetic data across the channel. Alternatively or additionally, processing system 150 may send periodic requests to one or more of force sensing module 130 and/or inertial measurement unit(s) 140a, 140b and receive updated kinematic and/or kinetic parameters in response to the requests. In either case, processing system 150 receives force and orientation information in real-time or near real-time.

Processing system 150 may be configured to determine a magnitude and/or location of the center of the force detected by force sensing module 130 (Step 1012). In certain embodiments, force sensing module 1340 may be configured to determine the location of the center of the force relative to the boundaries of the articular surface. In such embodiments, processing system 150 may not necessarily need to determine the location, since the determination was made by force sensing module 130.

In other embodiments, processing system 150 simply receives raw force information (i.e., a point-force value) from each sensor of force sensing module 130, along with data identifying which force sensor detected the particular force information. In such embodiments, processing system 150 may be configured to determine the location of the center of the force, by triangulating the center based on the relative value of a magnitude and the position of the force sensor within the force sensing module 130.

Processing system 150 may also be configured to determine an angle of flexion/extension of joint 120 based on the orientation information received from inertial measurement unit(s) 140a, 140b (Step 1014). For example, processing system 150 may be configured to receive pre-processed and error-corrected orientation information from the inertial measurement unit(s) 140a, 140b. Alternatively, processing system 150 may be configured to receive raw data from one or more of gyroscope 243, accelerometer 244, and/or magnetometer 245 and derive the orientation based on the received information using known processes for determining orientation based on rotation rate data from gyroscope, acceleration information from accelerometer, and magnetic field information from magnetometer. In order to enhance precision of the orientation information, data from multiple units may be used to correct data from any one of the units. For example, accelerometer and/or magnetometer data may be used to correct error in rotation rate information due to gyroscope bias and drift issues. Optional temperature sensor information may also be utilized to correct for temperature effects.

Once processing system 150 has determined the magnitude and location of the center of the force detected the force sensors and joint flexion/extension, varus/valgus, and internal/external rotation angles processing system 150 may analyze and compile the data for presentation in various formats that may be useful to a user of force sensing system 100 (Step 1022). For example, as shown in FIG. 10, processing system 150 may be configured to display the instantaneous magnitude and location of the center of the force (display area 940) on a portion of the GUI 900. According to one embodiment, software associated with processing system 150 may provide graphs 940a, 940b indicating the relative magnitude of the center of force detected at the respective sensors associated with medial and lateral portions 330a, 330b of the articular surface. As can be seen in FIG. 10, graphs 940a, 940b may include vertical gauges indicating the various force values that are detectable by processing system 150, along with a horizontal line that shows the instantaneous magnitude of the force value with respect to the gauge of possible values. As an alternative or in addition to graphs 940a, 940b, processing system 150 may be configured to simply display the numerical value of the medial and lateral forces, as shown in user interface elements 942a, 942b.

In addition to magnitude values, processing system 150 may include a user interface element configured to display the instantaneous locations 941a, 941b of the center of the medial and lateral forces relative to the boundaries of the articular surface. In addition to the location, the graphical element may also be configured to adjust the size of the cursor or icon used to convey the location information to indicate the relative magnitude of the force value. It should be noted that various other information can be provided as a user interface element associated with GUI 900.

For example, as an alternative or in addition to the magnitude and force presentation described above with respect to user interface region 940, processing system 150 may include user interface elements 950a, 950b, 950c that provides information indicative of the instantaneous values for flexion/extension (950b), internal/external rotation (950a), and varus/valgus alignment (950c), each of which processing system 150 can determine based on the 3-dimensional orientation information from inertial measurement unit(s) 140a, 140b (Step 1024). As part of this display element, processing system may also display graphical representations of femur 912a, tibia 912b, and force sensing module 930, based on the instantaneous position data received from inertial measurement unit(s) 140a, 140b. The graphical representation may consist of an artificial model of the knee representing an approximation of the patient's knee, animated in real-time as the joint angles change in response to articulation of the joint by the surgeon. Alternatively, in the case where 3D image of the patient's joint is available, an anatomically correct 3D model of the patient's knee may be created by the processing unit 150 and animated in real-time.

According to an exemplary embodiment, processing system 150 may also be configured to generate a user interface element 960 that displays data that tracks the magnitude (y-axis, 960b) medial and lateral force values 961a, 961b as a function of flexion/extension angle (x-axis, 960a) (Step 1026). User interface element 960 may provide both instantaneous and historical medial and lateral force magnitude data 960a as a function of flexion/extension angle 960a. This may be particularly helpful to the surgeon in evaluating how the force data changes as the joint is extended and flexed providing both kinematic and kinetic information.

Alternatively or additionally, processing system 150 may provide graphical output data on a user interface 970 associated with gap measurement module 800. According to one exemplary embodiment, user interface element 900 may include a chart 971 that provides respective gauges indicating the relative magnitude of medial and lateral gap distances 972a, 972b. Alternatively or additionally, chart 971 may include a field 973 that displays the location (medial/lateral) and value of a relative imbalance in the geometric gap at the tibiofemoral interface.

Figure 12:
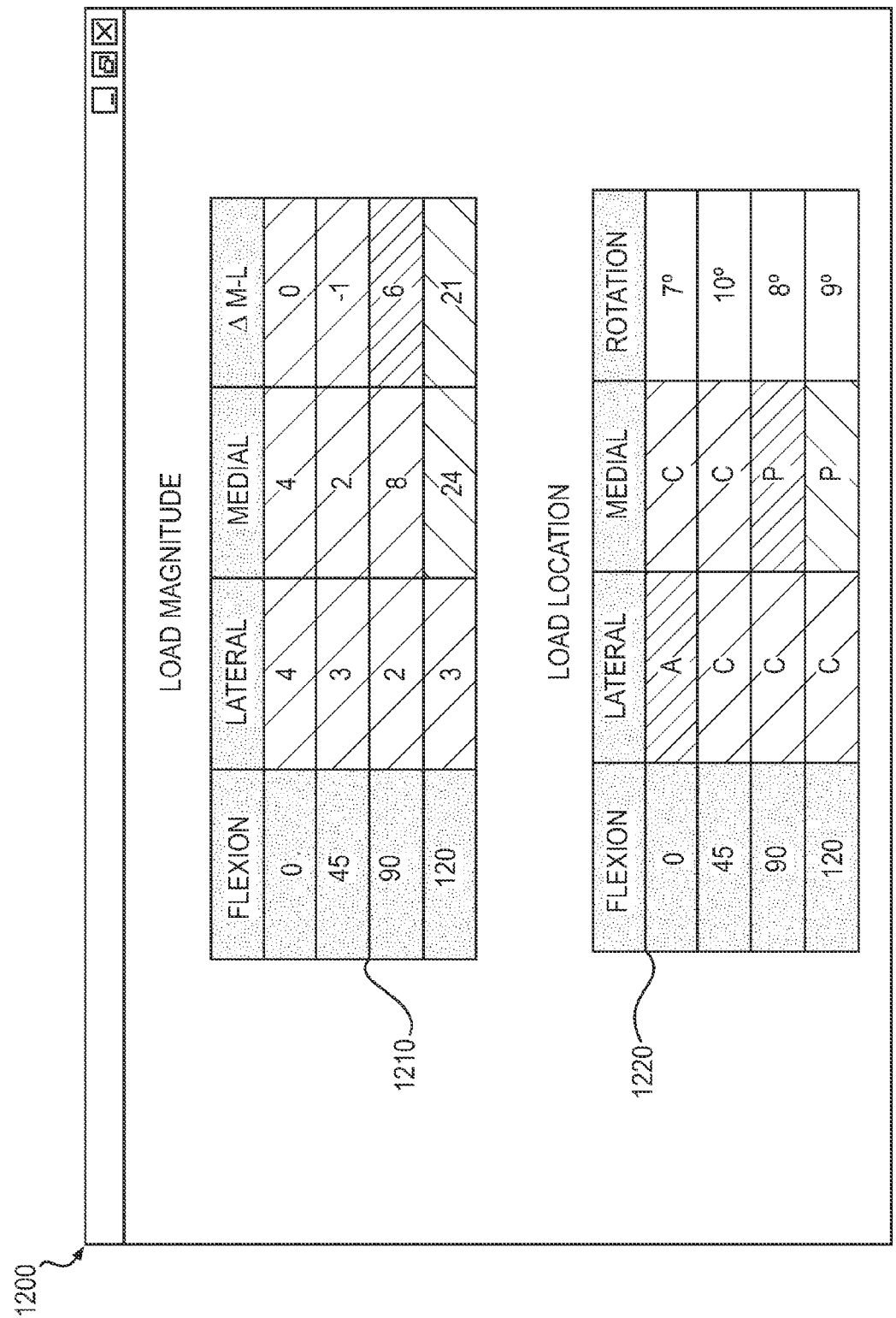
FIG. 12 provides an exemplary screen shot of a user interface, which may be provided on a monitor or output device, illustrating (in tabular form) load location and magnitude at different flexion angles, in accordance with the disclosed embodiments.

FIGS. 12-16 provide exemplary screen shots illustrating different ways that processing system 150 can present information to a user of knee balancing system 100. For example, FIG. 12 illustrates an exemplary screen shot 1200 that displays monitoring load magnitude and location information for predetermined angles of joint flexion. As illustrated in FIG. 12, processing system 150 can compile, in tabular form, the medial and lateral load magnitude data (as well as the difference information (illustrated as ΔD-L in FIG. 120) at flexion angles of 0°, 45°, 90°, and 120°. Processing system 150 can prepare this information for output on a display screen (of a computer or tablet device) in the operating room, so that the surgeon can evaluate the intra-operative performance of the knee joint.

According to another embodiment, processing system may compile, in tabular form, the medial and lateral load location information (relative to the anterior-posterior of force sensing module 130, as denoted by letters A, C, and P, where A is "anterior", C is "center", and P is "posterior") at flexion angles of 0°, 45°, 90°, and 120°. Processing system 150 may also determine the difference in rotation between the medial and lateral load centers with respect to medio-lateral axis of the knee. Processing system 150 can aggregate this information and render it for output on a display during the surgical procedure.

As an alternative or in addition to the tabular format illustrated in FIG. 12, processing system 150 may be configured to provide the medial and lateral load location and magnitude data overlaid atop a virtual representation of force sensing module 150. In the exemplary screen shot 1300, processing system 150 can provide user interfaces 1310, 1320, 1330, and 1340, which contains substantially the same information illustrated in the exemplary screen shot 1200 of FIG. 12, except the information is graphically overlaid atop an image representation of force sensing module 130.

Figure 13:
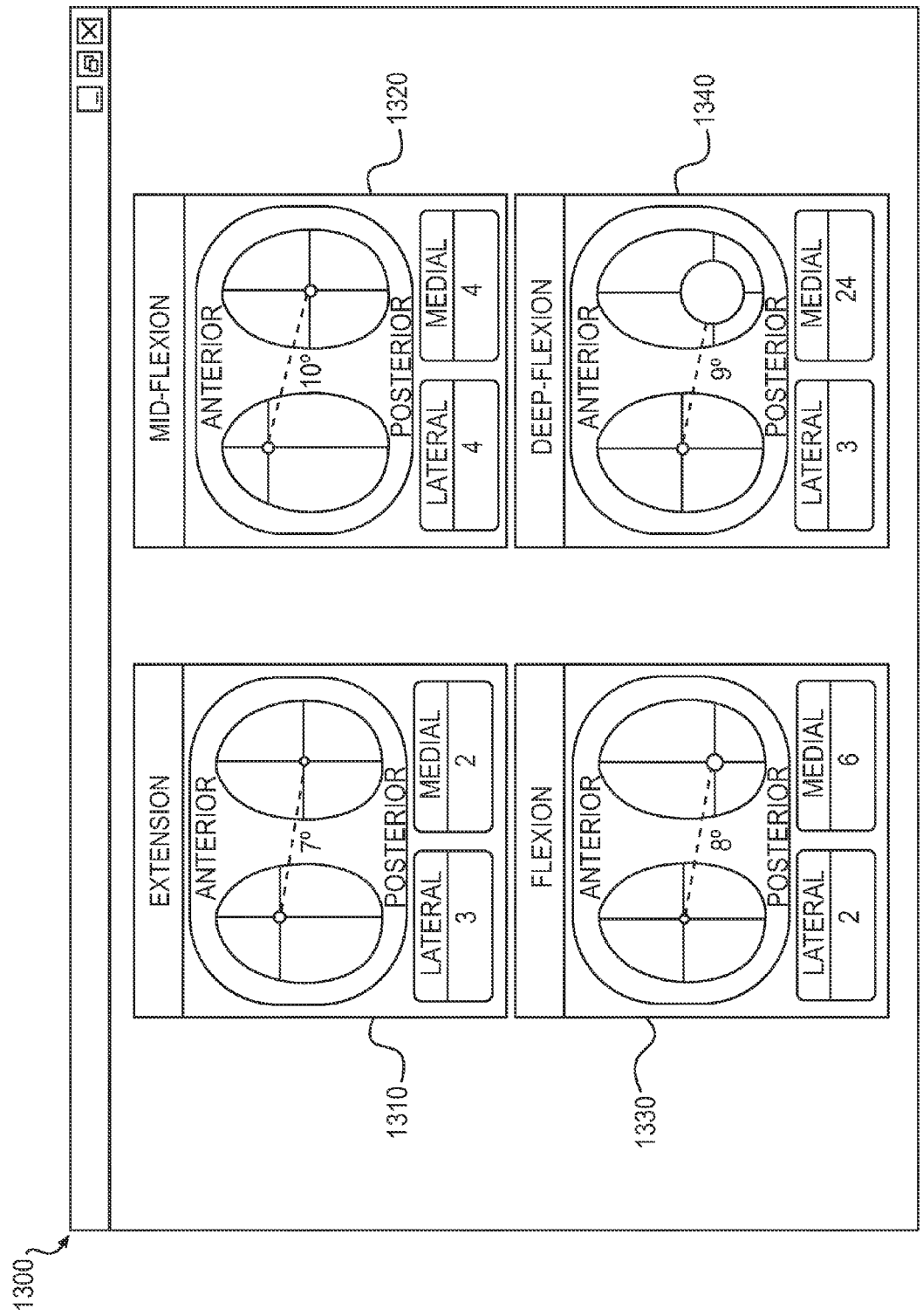
FIG. 13 provides another exemplary screen shot of a user interface, which may be provided on a monitor or output device, illustrating (in diagrammatic form relative to the force sensing module) load location and magnitude parameters in real-time, consistent with certain disclosed embodiments.
Figure 14:
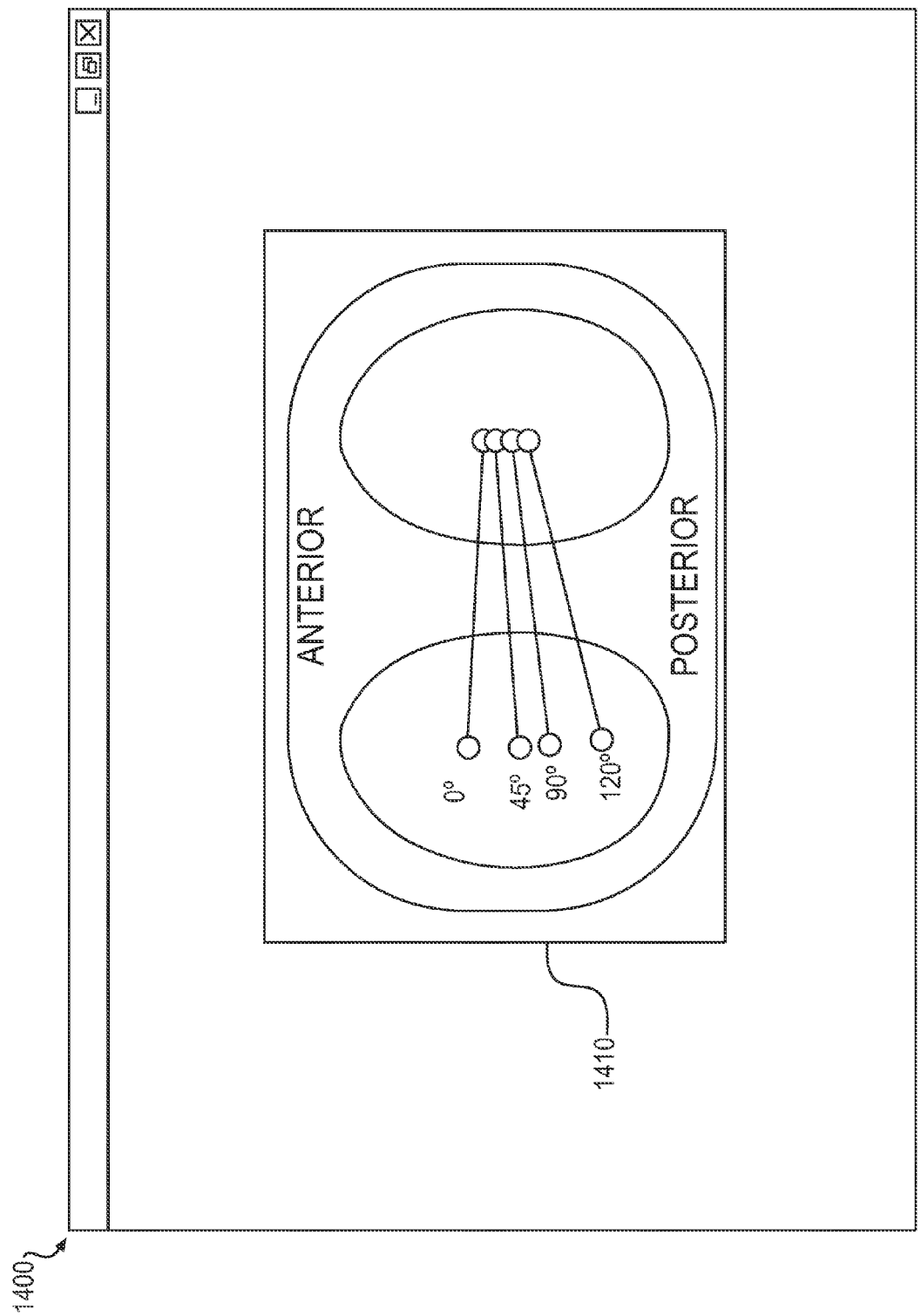
FIG. 14 provides an exemplary screen shot of a user interface, which may be provided on a monitor or output device, illustrating (in diagrammatic form relative to the force sensing module) load location and magnitude at pre-determined flexion angles, in accordance with the disclosed embodiments.

FIG. 14 provides an exemplary screen shot 1400 that provides a summary view of the magnitude and anterior-posterior location of the load at predetermined flexion angles. As illustrated in FIG. 14, processing system 150 may provide a user interface that illustrates the location of the load center detected in both the medial and lateral portions of force sensing module 130 at flexion angles of 0°, 45°, 90°, and 120°. Whereas screen shot 1300 of FIG. 13 illustrates this information in separate user interfaces 1310, 1320, 1330, and 1340, screen shot 1400 provide this information in a single, "summary"-type format, with circle sizes and/or colors used to denote the load magnitude instead of printed values.

Figure 15:
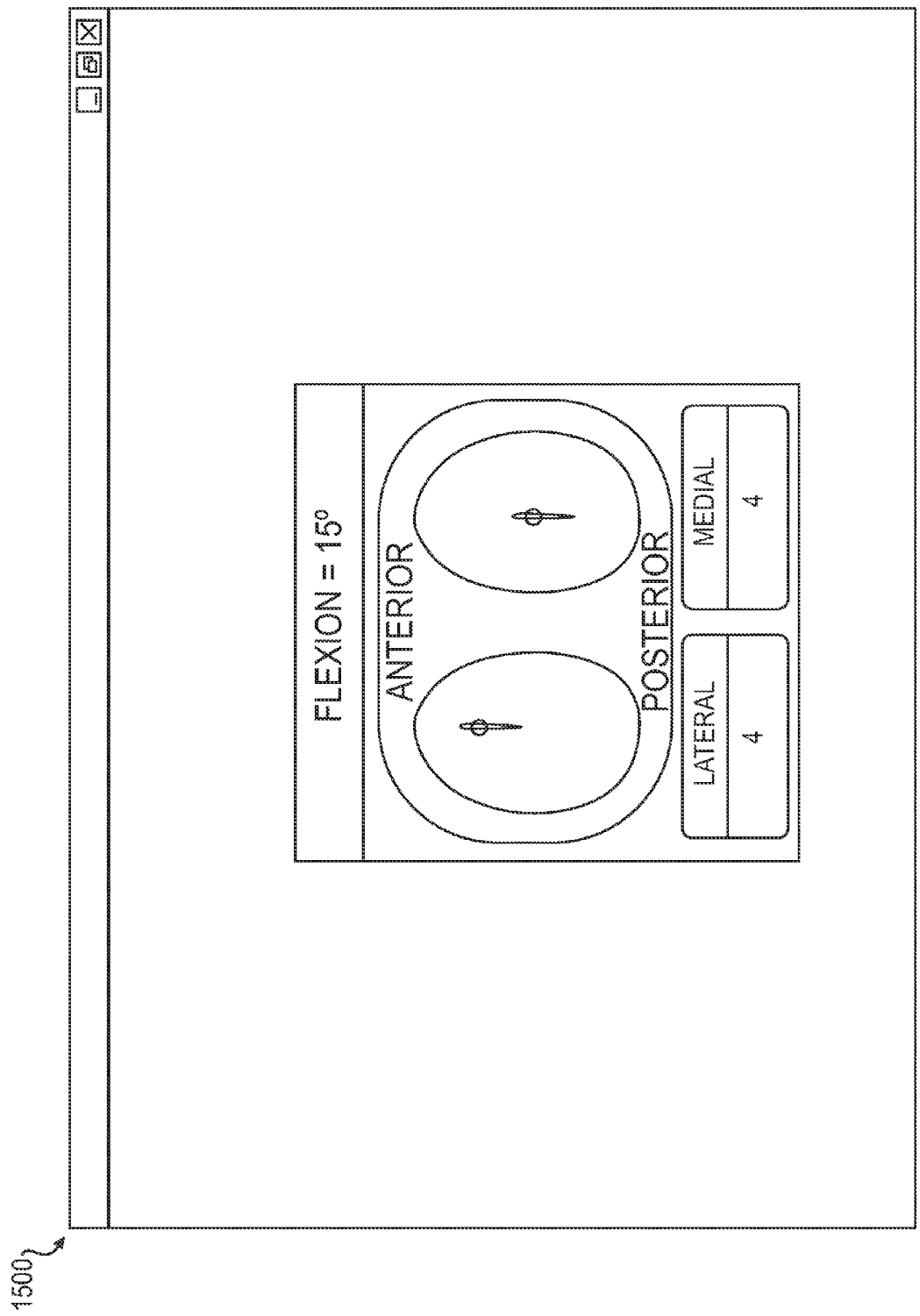
FIG. 15 provides an exemplary screen shot of a user interface, which may be provided on a monitor or output device, illustrating (in diagrammatic form relative to the force sensing module) current and historic load location and magnitude parameters, consistent with certain disclosed embodiments.
Figure 16:
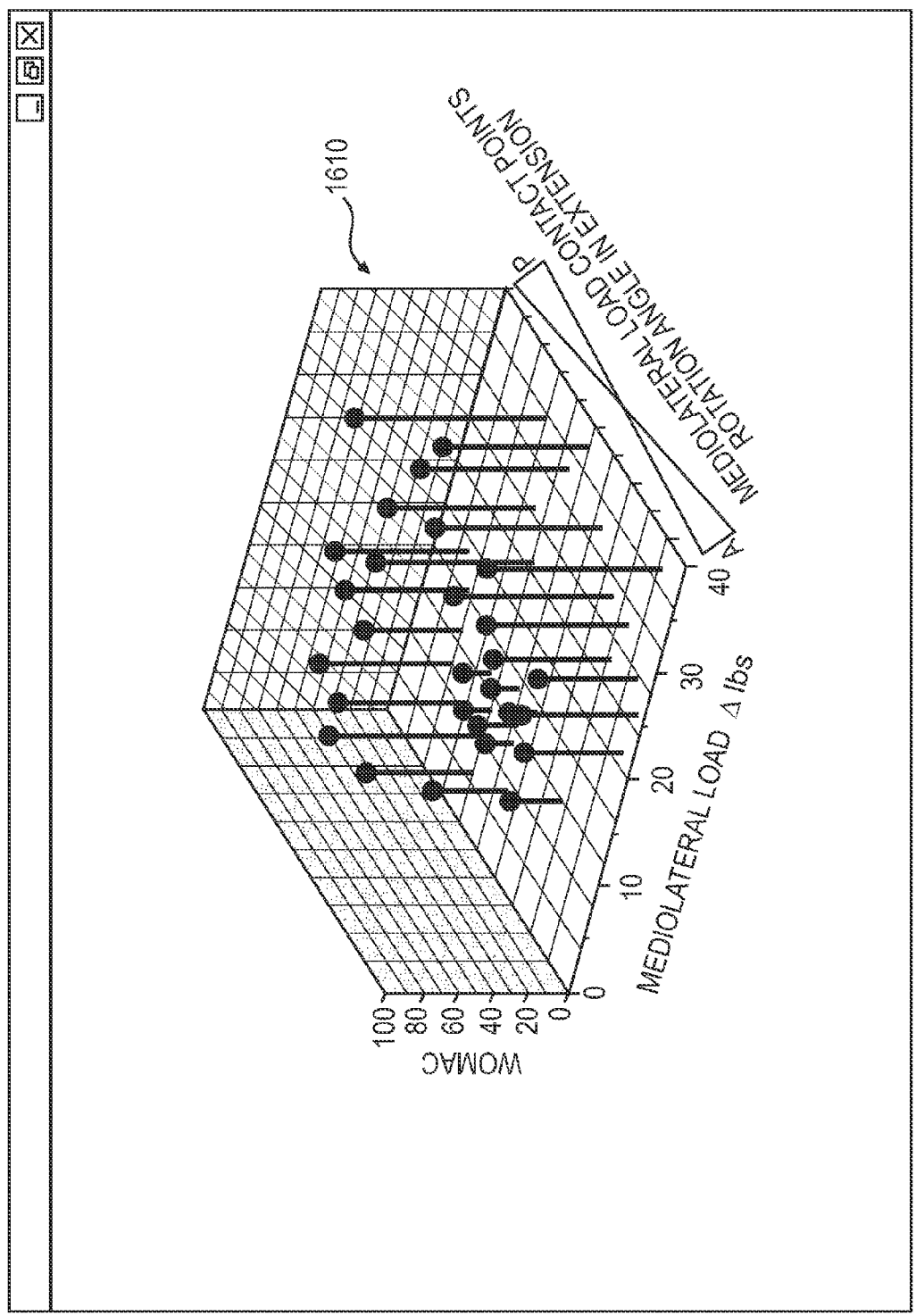
FIG. 16 provides an exemplary screen shot of a user interface, which may be provided on a monitor or output device, providing exemplary aggregated information on the relationship between load magnitude and location and overall patient satisfaction (as measurement by the WOMAC index), in accordance with the disclosed embodiments.

FIG. 15 provides an exemplary screen shot 1500 that provides both instantaneous tracking information of load location and magnitude, as well as historic information as the joint is flexed and extended. For example, processing system 150 may display the instantaneous (i.e., real-time) relative magnitude (indicated by the numerical chart below the graphical representation of the force sensing module 130), location information (indicated by the "circles" in the medial and lateral portions of force sensing modules), and flexion angle (15°). In addition, certain previously-measured data (such as the location data) may be tracked and overlaid in the medial and lateral portions of the user interface, to provide the surgeon with a view of the amount by which the location of the center of the load changes as the joint is flexed and extended.

Processing system 150 may also be configured to post-operatively aggregate results for a number of different patients that were measured during intra-operative analysis of the knee joint. For example, screen shot 1600 illustrates an exemplary user interface 1610 that displays intra-operative load data at various flexion/extension angles for a number of different patients. This data can be coupled with post-operative surveys in order to ascertain correlations between the intra-operative load testing data and final joint performance and patient satisfaction information (in this embodiment, using the WOMAC index). This type of analysis may be particularly useful in allowing surgeons to identify, using information for a variety of patients, specific load balance combinations and tolerances that result in maximum patient comfort and performance.

It will be apparent to those skilled in the art that various modifications and variations can be made to the disclosed systems and associated methods for measuring performance parameters in orthopedic arthroplastic procedures. Other embodiments of the present disclosure will be apparent to those skilled in the art from consideration of the specification and practice of the present disclosure. It is intended that the specification and examples be considered as exemplary only, with a true scope of the present disclosure being indicated by the following claims and their equivalents.

What is claimed is:

1. A force and orientation sensing system for measuring performance parameters associated with an orthopedic articular joint, comprising:
a force sensing module comprising:
a housing including an articular surface having a medial portion and a lateral portion, each of which is substantially mechanically isolated from the other;
a first set of sensors disposed within the housing, the first set of sensors being mechanically coupled to the medial portion of the articular surface and configured to detect information indicative of a first force incident upon the medial portion of the articular surface; and
a second set of sensors disposed within the housing, the second set of sensors being mechanically coupled to the lateral portion of the articular surface and configured to detect information indicative of a second force incident upon the lateral portion of the articular surface, and
an orientation sensing module comprising a first orientation sensor and a second orientation sensor, wherein the orientation sensing module is configured to detect, via the first and second orientation sensors, a relative orientation of at least two bones associated with the articular joint, and wherein each of the first and second orientation sensors comprises a gyroscope configured to detect a rate of angular rotation.

2. The force and orientation sensing system of claim 1, further configured to estimate, based at least in part on force values detected by the first set of sensors, a magnitude and a location of a center of force associated with the first force incident upon the medial portion of the articular surface.

3. The force and orientation sensing system of claim 1, wherein the second set of sensors includes a plurality of transducers, each transducer including:
a respective cantilever component at least a portion of which is configured to deform in response to the second force incident upon the lateral portion of the articular surface; and
a respective strain gauge coupled to the respective cantilever component and configured to measure the deformation in the respective cantilever component;
wherein at least a portion of each cantilever component associated with the plurality of transducers is mechanically supported at a proximal end by a central base component.

4. The force and orientation sensing system of claim 1, further comprising a wireless transceiver configured to wirelessly transmit the information indicative of the first and second forces to a remote processing module.

5. The force and orientation sensing system of claim 1, wherein at least one of the first and second orientation sensors are located outside the articular joint.

6. The force and orientation sensing system of claim 1, wherein the orientation sensing module is located outside the articular joint.

7. The force and orientation sensing system of claim 1, wherein the orientation sensing module is configured to detect, via each of the first and second orientation sensors, a respective relative orientation of a bone with respect to a reference orientation.

8. The force and orientation sensing system of claim 7, wherein the orientation sensing module is further configured to detect an angular relationship between the at least two bones associated with the articular joint.

9. The force and orientation sensing system of claim 8, wherein the angular relationship is at least one of a flexion-extension angle, a varus-valgus angle, or a rotation angle.

10. The force and orientation sensing system of claim 8, further comprising a processing device communicatively coupled to the orientation sensing module and configured to compute, based at least in part on the respective relative orientations of the bones, the angular relationship.

11. The force and orientation sensing system of claim 1, further comprising a processing device communicatively coupled to the force sensing module and the orientation sensing module and configured to:
estimate, based at least in part on the relative orientation detected by the first and second orientation sensors, a plurality of angular relationships between the at least two bones associated with the articular joint, and
provide the first and second forces incident upon the medial and lateral portions of the articular surface, respectively, in relation to each of the angular relationships between the at least two bones associated with the articular joint.

12. The force and orientation sensing system of claim 11, wherein the processing device is further configured to provide respective locations of a center of each of the first and second forces incident upon the medial and lateral portions of the articular surface, respectively, in relation to each of the angular relationships between the at least two bones associated with the articular joint.

13. The force and orientation sensing system of claim 1, wherein each of the first and second orientation sensors further comprises at least one of an accelerometer or a magnetometer.

14. The force and orientation sensing system of claim 13, further configured to correct, based on information detected by the at least one of the accelerometer or the magnetometer, angular rotation detected by the gyroscope.

* * * * *